US009612189B2

United States Patent
Hansen et al.

(10) Patent No.: US 9,612,189 B2
(45) Date of Patent: Apr. 4, 2017

(54) INTEGRITY MONITORING SYSTEM AND A METHOD OF MONITORING INTEGRITY OF A STATIONARY STRUCTURE

(75) Inventors: Henrik Roland Hansen, Slangerup (DK); Lars Højsgaard, Gadstrup (DK); Dirk Maiwald, Aldenhoven (DE)

(73) Assignees: NKT CABLES GROUP A/S, Brondby (DK); ENERGINET.DK, Fredericia (DK)

( * ) Notice: Subject to any disclaimer, the term of this patent is extended or adjusted under 35 U.S.C. 154(b) by 987 days.

(21) Appl. No.: 13/822,764

(22) PCT Filed: Nov. 3, 2011

(86) PCT No.: PCT/DK2011/050415
§ 371 (c)(1),
(2), (4) Date: Jul. 3, 2013

(87) PCT Pub. No.: WO2012/059108
PCT Pub. Date: May 10, 2012

(65) Prior Publication Data
US 2013/0275055 A1 Oct. 17, 2013

(30) Foreign Application Priority Data
Nov. 5, 2010 (DK) .................................. 2010 01005

(51) Int. Cl.
*G01B 3/52* (2006.01)
*G01N 29/00* (2006.01)
(Continued)

(52) U.S. Cl.
CPC ............. *G01N 19/00* (2013.01); *G01H 9/004* (2013.01); *G01M 3/007* (2013.01); *G01M 3/243* (2013.01);
(Continued)

(58) Field of Classification Search
CPC .... G01M 3/007; G01M 3/243; G01M 5/0025; G01M 5/0033; G01M 5/0066;
(Continued)

(56) References Cited

U.S. PATENT DOCUMENTS

| 4,536,861 A | 8/1985 | Graindorge et al. |
| 4,841,192 A | 6/1989 | Tetlie et al. |

(Continued)

FOREIGN PATENT DOCUMENTS

| CA | 2 270 066 A1 | 10/2000 |
| EP | 0 512 789 A2 | 11/1992 |

(Continued)

OTHER PUBLICATIONS

Extended European Search Report for 11 83 7602 dated Oct. 16, 2013.
(Continued)

*Primary Examiner* — An Do
(74) *Attorney, Agent, or Firm* — Pearne & Gordon LLP

(57) ABSTRACT

An integrity monitoring system for monitoring integrity of at least a part of a stationary structure includes a vibration sensor for sensing vibration as a function of time, a computer, transmitting means for transmitting vibration data from the vibration sensor to the computer, means for acquiring position as a function of time data of a movable object, such as a vessel, a vehicle or a digging tool. The movable object includes a transmitter transmitting the position as a function of time data to the computer when the movable object is within a selected distance to a monitoring site. The monitoring site includes the part of the stationary structure to be monitored and the vibration sensor is arranged to sense vibrations within the monitoring site. The computer includes hardware and software for comparing the vibration data with the position as a function of time data.

35 Claims, 9 Drawing Sheets

(51) Int. Cl.
*G01N 19/00* (2006.01)
*G01H 9/00* (2006.01)
*G01M 3/00* (2006.01)
*G01M 3/24* (2006.01)
*G01M 5/00* (2006.01)
*G01M 7/00* (2006.01)
*G01N 29/44* (2006.01)

(52) U.S. Cl.
CPC ........ *G01M 5/0025* (2013.01); *G01M 5/0033* (2013.01); *G01M 5/0066* (2013.01); *G01M 7/00* (2013.01); *G01N 29/4436* (2013.01); *G01V 2210/1429* (2013.01)

(58) Field of Classification Search
CPC ..... G01M 7/00; G01H 9/004; G01N 29/4436; G01N 19/00; G01V 2210/1429
USPC ............. 702/33–35, 51, 54, 56; 73/587, 592
See application file for complete search history.

(56) References Cited

U.S. PATENT DOCUMENTS

| | | | |
|---|---|---|---|
| 4,953,144 | A | 8/1990 | Chin |
| 4,958,329 | A | 9/1990 | Marschall |
| 5,136,549 | A | 8/1992 | Berglund |
| 5,227,624 | A | 7/1993 | Henning et al. |
| 6,082,193 | A | 7/2000 | Paulson |
| 7,369,459 | B2 | 5/2008 | Kawabata et al. |
| 7,415,117 | B2 | 8/2008 | Tashev et al. |
| 7,607,351 | B2 * | 10/2009 | Allison ............... F16L 55/00 702/36 |
| 7,668,670 | B2 * | 2/2010 | Lander ............... G01M 3/243 340/605 |
| 7,751,977 | B2 | 7/2010 | Winkler et al. |
| 8,296,083 | B2 * | 10/2012 | Martin ............... G01M 3/243 340/605 |
| 2007/0210929 | A1 | 9/2007 | Sabata |
| 2009/0000381 | A1 | 1/2009 | Allison |
| 2009/0132183 | A1 | 5/2009 | Hartog et al. |

FOREIGN PATENT DOCUMENTS

| | | |
|---|---|---|
| EP | 1 033 584 A2 | 9/2000 |
| EP | 2 006 654 A2 | 12/2008 |
| GB | 2462096 A | 1/2010 |
| WO | 03/100453 A1 | 12/2003 |

OTHER PUBLICATIONS

Japanese Office action for 2013-537004 dated Sep. 29, 2015.
Chinese Office action for 201180052425.1 dated Oct. 20, 2015.
Marinho, et al., "Surface Monitoring Techniques for a Continuous Flexible Riser Integrity Assessment", Offshore Technology Conference, 2007, Houston, TX.
Melve, "Acoustic Emission Monitoring of GRP Pipes and Tanks", Statoil Research Centre, Trondheim, Norway.
"Guidance Notice on Monitoring Methods and Integrity Assurance for Unbonded Flexible Pipes", Oil & Gas UK, Aug. 2010.
Denmark Search Report for PA 2010 01005 dated Aug. 8, 2011.

* cited by examiner

INTEGRITY MONITORING SYSTEM AND A METHOD OF MONITORING INTEGRITY OF A STATIONARY STRUCTURE

TECHNICAL FIELD

The invention relates to an integrity monitoring system for monitoring integrity of at least a part of a stationary structure offshore or onshore, such as a pipe or a power cable. The invention also relates to a method of monitoring integrity of at least a part of a stationary structure.

BACKGROUND ART

It is well known to use acoustic sensors for monitoring pipelines e.g. to observe a wire breakage or similar. An example of such monitoring system is for example described in U.S. Pat. No. 6,082,193. This monitoring system comprises an array of acoustic sensors spaced along a cable and deployed in a fluid filled concrete pipeline. The sensors are monitored to find acoustic anomalies, particularly anomalies resulting from breakage of a reinforcing wire for the concrete. The location of wire breaks can be found from the data collected.

Acoustic monitoring systems have also been applied offshore. U.S. Pat. No. 7,751,977 describes a system for avoiding collision between a vessel and a manmade structure, where an acoustic sensor is connected or placed near to the manmade structure. The data measured by the acoustic sensor is transmitted wireless to the vessel.

WO 03/100453 describes an acoustic monitoring system with a number of hydrophones. By help of acoustic measurements the system can discover imbalances, vibrations and leakage. US 2009/0132183 describes a technique for monitoring a pipeline operatively connected to an optical fiber. The optical fibre may e.g. combine the observance of Brillouin backscatter and coherent Rayleigh noise.

EP 2006 654 discloses several methods for acoustic sensor leak detection of transmission and distribution pipes using hydrophones.

In many situations the prior art acoustic sensor systems work well. However, in general there is a need for an improved monitoring system for monitoring the integrity of a stationary structure and in particularly for integrity monitoring of stationary structures which should remain in position for a long time, such as several years.

DISCLOSURE OF INVENTION

The object of the invention is to provide an integrity monitoring system for monitoring integrity of at least a part of a stationary structure, which integrity monitoring system provides high security for the stationary structure and which integrity monitoring system simultaneously can be provided at relatively low cost compared to its high beneficial effect.

The integrity monitoring system of the invention is defined in the claims and in the following description, examples and drawings.

Further advantages of the invention and of embodiments thereof will be clear from the dependent claims as well as from the following description, examples and drawings.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

All features of the invention including ranges and preferred ranges can be combined in various ways within the scope of the invention, unless there are specific reasons for not to combine such features.

A core feature of the integrity monitoring system of the invention is that the integrity monitoring system is arranged to or capable of obtaining data from at least two different sources and combining and/or comparing these data. The integrity monitoring can thereby in a very simple manner be very reliable. Furthermore the integrity monitoring system can be provided and operated in an economically attractive way for monitoring at least a part of a stationary structure.

The term "stationary structure" is used herein to mean any solid structure which in an undamaged condition is held in a generally stationary position optionally subjected to limited movements due to natural environmental influences e.g. by wind and/or water. If for example the stationary structure is a submarine structure changes in the seabed e.g. by moving sediments e.g. sand dunes may in one embodiment lead to free flooding of the stationary structure e.g. when vibrations are induced by underwater currents. Further examples of stationary structures are given below.

In the following the term "stationary structure" comprises the whole or a part of the stationary structure unless other is specifically stated.

The Integrity monitoring system of the invention for monitoring integrity of at least a part of a stationary structure comprises at least a vibration sensor;

a computer;

transmitting means for transmitting vibration data from the vibration sensor to the computer; and means for acquiring and transmitting position as a function of time data.

It should be noted that the integrity monitoring system may comprise additional elements and/or functions as described below.

Furthermore, it should be noted that the computer may be integrated in any other elements of the integrity monitoring system, for example the computer or a part thereof may be integrated with the vibration sensor. The computer may be any kind of computing device or part of a device. A computer is herein defined as a device that is capable of computing data. In other words, the computer can receive data and can be programmed to perform calculations using the received data. The computer may be a programmable machine that can receive input data, manipulate the data, and provide an output in a useful format. A memory is usually an integrated part of the computer or it is in data communication with a computer. The computer preferably operates using digital operation system(s), and preferably uses integrated circuit technology and comprises microprocessors. In most situations it is preferred that the computer is or comprises a PC or a part thereof wherein one or more computing elements may be incorporated into another element or other elements of the system e.g. by being embedded in such other element(s).

"Data" means any kind of data, but in most situations will be in the form of digital data signal or analog data signal or a combination e.g. converted using a graphic card or other data converting elements.

"Position as a function of time data" will also be referred to as "position (h)" and means a physical position to a given time. The position may be in relation to the submarine structure or in geographical coordinates. The time may be in the form of time passed from a known (e.g. selected) starting point or it may be in a standard time such as nautical standard time or UTC (Coordinated Universal Time) or other standard time zones.

"Integrity monitoring" means that the monitoring is at least capable of detecting if the part of the submarine structure to be monitored is severely damaged, such as damage that obstacles its ordinary operation. Preferably the integrity monitoring is sufficiently sensitive to even monitor lesser damage to the submarine structure or even prevent damage by monitoring parameter indicating increased risk of damage of the submarine structure.

"Vibrations" should herein be construed to mean vibrations of any wavelength, but in particular acoustic vibrations, which herein should be construed to mean mechanical waves in liquids, and optionally in solids.

The integrity monitoring system comprises at least one vibration sensor for sensing vibration as a function of time, a computer, transmitting means for transmitting vibration data from the vibration sensor to the computer, means for acquiring and transmitting position as a function of time data of a movable object comprising a transmitter to the computer when the movable object is within a selected distance to a monitoring site, where the monitoring site comprises the part of the stationary structure and the vibration sensor is arranged to sense vibrations within the monitoring site, the computer comprises hardware and software for comparing the vibration data with the position as a function of time data.

The movable object can in principle be any kind of movable object which comprises a transmitter such that its position as a function of time data can be transmitted to the computer, directly or via one or more other elements e.g. comprising a satellite, the Internet one or more wireless transmissions, global position elements or other transmitting elements. The movable object may for example be a vehicle, an airplane, a motorized tool or a vessel. Further examples will be provided below.

In one embodiment the stationary structure is a substantially fixed structure, such as a structure applied in a stationary manner and/or laid on the ground and/or seabed and/or buried and/or a trenched stationary structure.

"Substantially fixed" means that the stationary structure is not actively subjected to movements i.e. it is not connected to or comprises a motorized unit. Preferably the substantially fixed submarine structure is not subjected to movements beyond a distance of +− about 20 m, more preferably the substantially fixed submarine structure is not subjected to movements beyond a distance of +− about 10 m, even more preferably the substantially fixed submarine structure is maximally subjected to movements up to a distance of +− about 5 m. The fixing may e.g. be provided by an anchor or anchor structure, one or more bolt/nut systems or other fixing elements that limit or obstruct movements of the stationary structure.

In one embodiment the substantially fixed structure is subjected to passive movement provided by unstructured influences from the environment, e.g. provided by influence from wind or water directly or indirectly.

In one embodiment wherein the stationary structure is a substantially fixed structure, the structure is applied in a stationary manner by being a submarine structure laid on the seabed or buried and/or a trenched submarine structure or by being a buried non-submarine structure.

"A submarine structure" means herein a structure or the part of a structure which is arranged below sea surface, such that at least the part of the submarine structure to be monitored for its integrity is applied below sea surface.

"A non-submarine structure" means herein a structure or the part of a structure which is not a submarine structure as defined above, such that at least the part of the non-submarine structure to be monitored for its integrity is applied above sea surface.

Accordingly a stationary structure may comprise both a submarine structure and a non-submarine structure if a part of the stationary structure which is to be monitored for its integrity is above sea surface and another part of the stationary structure which is to be monitored for its integrity is below sea surface.

The term "trenched" is used to specify that the submarine structure is applied in a ditch, but not fully covered with sediment. The term "buried" is used to specify that the stationary structure e.g. the submarine structure is fully covered with sediment, sand, stone, concrete and/or asphalt.

The term "sediment" means any solid material that has been or is being eroded, transported and deposited. The term "cover material" is a common name for material that covers or may cover the stationary structure and includes sediment, sand, stone, concrete and/or asphalt.

In order to obtain a substantial benefit from applying an integrity monitoring system of the invention, the stationary structure may preferably be a structure which is at least partly in risk of being damaged by a movably object or a part thereof or a part connected to or movable with the movable object.

Furthermore, the stationary structure may be partly or totally hidden from visual monitoring or it may have at least one large dimension which may make it difficult or expensive to monitor visually.

In one embodiment the stationary structure is an elongate structure with a length dimension which is at least about 100 times its largest dimension determined perpendicular to its length dimension. The stationary structure may preferably have a length of at least about 10 m, such as at least about 100 m.

The integrity monitoring system is particularly beneficial in the situation where the stationary structure is or comprises a cable, a pipe and/or an optical fibre. Cables, pipes, optical fibres and combinations thereof are often fairly long, difficult or expensive to monitor visually and may in many situations be subjected to damage by moving parts such as moving objects or a part thereof or a part connected to or movable with the movable object. The integrity monitoring system of the invention in particular provides a beneficial solution for the monitoring of cables, pipes, optical fibres and/or combinations or parts thereof.

In one embodiment the stationary structure optionally is or comprises a cable bundle.

A cable bundle consists of two or more different types of cables, pipes and/or fibres. They may be more or less integrated with each other, e.g. being bundled to each other at least in two or more positions along their length or they may be fully integrated e.g. in a conduit, an umbilical or similar outer covering layer.

In one embodiment where the stationary structure is a submarine structure, the submarine structure is a flow line applied in a substantially horizontal direction.

In one embodiment where the stationary structure is a submarine structure, the submarine structure is a riser applied in a substantially vertical direction.

Such submarine structures are well known in the art and will not be described in further details herein.

In one embodiment the stationary structure is a transferring stationary structure, such as a stationary structure capable of transmitting power and/or electromagnetical waves and/or a stationary structure capable of transporting a flowable medium such as a fluid e.g. a hydrocarbonous fluid and/or water.

Electromagnetical waves mean electromagnetic radiation with any frequency of wave(s). The electromagnetical waves may for example be radio waves, microwaves, infrared radiation, visible light, ultraviolet radiation, X-rays and gamma rays. The electromagnetical waves may preferably have wavelengths of about 10 nm or more. For optical fibres the wavelength will normally be from about 10 nm to about 2000 nm, and preferably within 400 nm to 1600 nm. In one embodiment the wavelength may preferably be radio waves (from about 1 m and longer) or microwaves (from about 1 m to about 1 mm).

Integrity monitoring of a transferring stationary structure provides an important security, and may even result in prevention of damage due to leakage and spill of hydrocarbons, and/r loss of supplying gas, water or power which may be costly e.g. to factories, hospitals and other and/or cause nuisance to ordinary households. Due to the integrity monitoring system of the invention damage may be predicted and the transferring stationary structure may be shut down and/or be replaced before a total burst of the transferring stationary structure.

The integrity monitoring system may in one embodiment provide the option of repairing a slightly damaged transferring stationary structure to prevent burst thereof, and thereby prolong the life time of the transferring stationary structure.

In one embodiment the stationary structure comprises a cable, such as a signal and/or a power transmission cable, preferably selected from a high voltage electric power cable (Above about 72 kV e.g. up to about 550 kV or even higher), a medium voltage electric power cable (about 10-72 kKV), a super conducting cable, an optical fibre cable and/or a communication cable.

In one embodiment the stationary structure comprises a pipe, such as a pipe for transporting fluids, such as water, gas and/or hydrocarbons e.g. crude oil.

Accordingly prevention of spill of fluids may be provided as a result of the integrity monitoring system of the invention.

The vibration sensor may in principle be any kind of sensor which has a sufficient sensitivity to sense vibrations for providing an integrity monitoring of the stationary structure or the part thereof to be monitored. Vibration sensors are generally known to a skilled person in the art, and the skilled person will be able to find a suitable vibration sensor or sensors for a given integrity monitoring system, e.g. by contacting a producer of vibration sensors. In the selecting of the vibration sensor(s) the skilled person may for example consider the sensitivity of the vibration sensor e.g. for different types of vibrations/noise, the cost of the vibration sensor, the predicted life time of the vibration sensor, the accuracy of the vibration sensor as well as the size thereof and possible ways of getting output from the vibration sensor. Examples of preferred sensors e.g. for given applications of the integrity monitoring system are provided below.

In one embodiment the vibration sensor is an acoustic sensor. Acoustic sensors are generally known in the art and are used for many different applications. The vibration sensor may preferably comprise a microphone, a hydrophone, a seismometer and/or an optical fibre acoustic sensor.

In one embodiment the vibration sensor operates continuously and an output signal can be obtained continuously over time. Many types of vibration sensors are suitable for such continuous operation, but may also be applied for operating at predetermined intervals, upon impact and/or upon vibrations above a certain selected db level.

In one embodiment the vibration sensor operates at predetermined intervals.

In one embodiment the integrity monitoring system comprises a regulating function for regulating the operation of the vibration sensor.

The regulating function may be for example be an automatically, semi-automatically or a settable regulating mechanism applied to regulate the activity and/or the sensitivity of the vibration sensor.

For saving power (e.g. battery power) the regulating function may in one embodiment be automatically regulated in relation to activity. In most situations, however, a power saving mode would not make much sense, namely in situations where all active components are placed on-shore and no battery based system is involved. Generally the required amount of power is relatively low even without a power saving mode.

In one embodiment the regulating function is an automatically or semi-automatically regulating mechanism, regulating the sensitivity of the vibration sensor. Generally, noise in the environment around the stationary structure and also within the monitoring site will not be constant over time and not be homogenous along the complete stationary structure. In order to have a suitable sensitivity it is therefore beneficial if the vibration sensor comprises such automatically or semi-automatically regulating mechanism for filtering noise. The automatically or semi-automatically regulating mechanism may for example comprise a range and time dependent gain control for taking account of changes in background noise levels along the stationary structure and/or over time.

For increased security the integrity monitoring system may in one embodiment comprise one or more redundant vibration sensors. This/these one or more redundant vibration sensors may be applied to replace malfunctioning vibration sensors and/or for testing active vibration sensors e.g. for calibrating an active vibration sensor. The redundant sensor or sensors may be equal to or different from the vibration sensor(s) it/they are supposed to replace and/or test. Generally it is simpler if the redundant sensor or sensors is/are selected to be substantially equal to or at least of similar type as the vibration sensor(s) the redundant sensor or sensors are supposed to replace and/or test. In one embodiment the redundant sensor or sensors is/are selected to be of a lower quality than the vibration sensor(s) the redundant sensor or sensors are supposed to replace and they are adapted merely to be used while the original vibration sensor(s) is/are being replaced.

The redundant sensor or sensors may preferably be placed immediately adjacent to the vibration sensor(s) they are adapted to replace and/or test.

In one embodiment the redundant sensor or sensors is/are placed at a distance from the vibration sensor(s) they are adapted to replace and/or test. If for example the vibration sensor is an integrated vibration sensor, the redundant vibration sensor may be a non-integrated vibration sensor.

The vibration sensor may in principle be placed anywhere in relation to the stationary structure, provided that it is capable of sensing vibrations within the monitoring site comprising at least the part of the stationary structure to be monitored. The optimal place for the vibration sensor(s)

depends largely on the type of stationary structure to be monitored and where the monitoring shall be performed. Furthermore, some arrangements of the vibration sensor(s) have shown to provide additional benefits as it will be explained later on.

In one embodiment the system comprises a vibration sensor which is arranged in direct contact with the stationary structure for monitoring vibrations of the stationary structure itself. In relatively noisy environments it may be very beneficial to arrange the vibration sensor in direct contact with the stationary structure for monitoring vibrations of the stationary structure itself. Thereby it may be simpler to filter off noise and a more correct integrity monitoring of the stationary structure may be obtained. Furthermore, in situations where the vibration sensor may itself be very exposed to damage, the vibration sensor may be protected by being in direct contact—e.g. by being integrated in—the stationary structure.

In one embodiment the system comprises a vibration sensor which is arranged not to be in direct contact with the stationary structure. This embodiment may have the additional benefit that a very accurate determination between the stationary structure and the movable object may be obtained. For example the integrity monitoring system may be arranged to start an alarm if a movable object is passing a vibration sensor. If for example the stationary structure is a buried water pipe and the sensor is buried above e.g. 10 cm above the water pipe, and the moving object is a drilling tool, a warning may be emitted if the operating drill comes too close to the water pipe, while still avoiding emitting false warnings merely because the drilling tool is near the water pipe.

In one embodiment the vibration sensor comprises at least one hydrophone, such as a conventional electrical hydrophone or a fibre laser hydrophone. This is in particular beneficial in a situation where the vibration sensor is to operate in wet or moist environment, for example in offshore environment.

A hydrophone will in particular be applied for off-shore systems where the stationary structure is a submarine structure. A hydrophone is a point sensor. Such sensors are well known in the art and will not be described in further detail herein. In one embodiment the hydrophone is a fibre laser hydrophone. Such fibre laser hydrophone allows for a very long optical signal (connection) cable. But it is still a point sensor. Examples of useful hydrophones are e.g. described in U.S. Pat. No. 5,227,624, U.S. Pat. No. 4,536,861, U.S. Pat. No. 4,841,192, U.S. Pat. No. 4,958,329 and U.S. Pat. No. 5,136,549.

In one embodiment the vibration sensor is a distributed vibration sensor.

A distributed sensor such as a fibre sensor provides the advantage that a long range for example such as 1 km or longer e.g. even up to several hundred kilometers, such as 5-100 km or 10-50 km can be monitored with one sensor. Accordingly a distributed vibration sensor is very beneficial to use in the integrity monitoring system in the situation where the stationary structure to be monitored is relatively long. The processing of the data obtained by a distributed vibration sensor may, however, require complex programming of the computer. Software for such data processing is however available and can—without undue burden—be selected by a skilled person. Often the necessary software for a given distributed vibration sensor is sold together with the distributed vibration sensor.

In one embodiment the vibration sensor comprises an optical fibre sensor, the optical fibre sensor is preferably arranged to operate by backscattering effect, such as Brillouin Backscattering, Raman Backscattering or Rayleigh Backscattering.

In one embodiment the optical sensor operates using polarization properties of the optical fibre, preferably such that the polarization properties of the backscattered signal are used to detect deformations, if any (e.g. by acoustic waves) of the fibre.

In one embodiment the vibration sensor comprises a Fibre Bragg Gratings (FBGs) sensor.

All the above mentioned types of vibration sensor are well known in the art.

The transmitting means for transmitting vibration data from the vibration sensor to the computer may be any kind of means which may or may not be integrated in any of the elements/objects of the integrity monitoring system or which may be provided wholly or partly by an external element, such as the internet. Today it is well known that data can be transmitted by a plurality of different ways, including digital transmission means.

In one embodiment the vibration sensor is integrated with or directly connected to the transmitting means. The vibration sensor may for example be directly connected to the computer and the transmission means is provided by the direct connection, and/or the vibration sensor comprises a transmitter e.g. a blue tooth transmitter or a long range transmitter. The vibration sensor may in this embodiment preferably be an optical fibre sensor.

In one embodiment the computer is not directly connected to the vibration sensor. In this embodiment the computer is optionally a remote computer arranged at a distance of the vibration sensor which distance in principle may be any distance. In one embodiment the computer is a remote computer arranged at a distance of the vibration sensor which is at least about 1 m, such as at least about 5 m, such as at least about 100 m, such as up to about 100 km or even more.

The computer may for example be a central integrity monitoring computer which connects several integrity monitoring systems where at least one of the integrity monitoring system is according to the present invention. Thereby it is possibly to provide a central integrity monitoring of many stationary structures placed anywhere in the world. In this embodiment it is preferred that the transmitting means for transmitting vibration data from the vibration sensor to the computer preferably comprises transmitting data via the internet.

In one embodiment the computer is directly connected to the vibration sensor and the vibration sensor is a fibre vibration sensor and the directly connecting provides at least a part of the transmitting means.

In one embodiment the transmitting means for transmitting vibration data from the vibration sensor to the computer comprises a wireless transmission and/or a transmission via an optical fibre and/or a Power-Line-Communication (PLC), the wireless transmission may e.g. be a radio or microwave frequency transmission comprising both long range transmissions and short range transmissions (blue tooth).

In one embodiment the means for transmitting vibration data from the vibration sensor to the computer comprises a recording medium. In this embodiment the transmitted vibration data comprises the vibration as a function of time and the vibration as a function of time data is delayed, for example with a delay time of about 10 minutes to about 30 days, such as from about 1 hour to about 24 hours.

In the above embodiment where the means for transmitting vibration data from the vibration sensor to the computer comprises a recording medium, the integrity monitoring system may operate by recording vibration as a function of time and transmitting the recorded data to the computer e.g. wireless with a time delay. In one embodiment the integrity monitoring system operates by recording vibration as a function of time on a first recording medium for a certain length of time, terminating recording on the first recording medium and transmitting the recorded data to the computer e.g. wireless or e.g. by physically connecting the first recording medium (which may be a movable recording medium) to the computer. The system may be operated such that the transmission of the recorded data on the first recording medium to the computer is conditioned on position as a function of time data of a movable object transmitted to the computer and/or on the possible malfunction/damage observed on the stationary structure. At the time or overlapping with the time of terminating recording on a first recording medium, recording on another recording medium may e.g. be started to obtain a full recording.

In that way not all vibration data needs to be transmitted to the computer but the vibration data can later on be examined for example in case of earlier incidents e.g. damage to the stationary structure or the vibration data can be checked at a later stage for other reasons.

The transmitting means for transmitting vibration data from the vibration sensor to the computer may be arranged to transmit vibration as a function of time data, in particular if the vibration data is transmitted with a delay. However, the vibration data may in one embodiment be transmitted without time data. In the latter situation the time connected to the respective vibration data is generated by the system preferably by the computer. This may in particular be beneficial if the vibration data is transmitted without delay or if the length of the delay is known e.g. if it is a constant time delay.

In one embodiment the integrity monitoring system comprises a recording medium for recording the transmitted vibration data as a function of time. This recording may be used for statistics for calibration and/or for later examination of an incident.

The means for acquiring and transmitting position as a function of time data of a movable object may comprise any means and combinations thereof. As mentioned above, transmission of data, in particular in digital or analog form is well known and a lot of systems/methods can be applied by a skilled person without undue burden, but merely by using ordinary skill.

Generally it is desired that the means for acquiring and transmitting position as a function of time data of a movable object comprising a transmitter, comprises a wireless transmitting means.

In one embodiment the means for acquiring and transmitting position as a function of time data of a movable object comprises a receiver capable of receiving the position as a function of time data directly from the transmitter (for example using a VHF transmitter) of the movable object, via internet transmission, via satellite and/or via and/or via an external antenna. The receiver may optionally be an integrated part of the computer or be in wireless or optical fibre communication with the computer.

In one embodiment the means for acquiring and transmitting position as a function of time data of a movable object comprises a recording medium. In this embodiment transmitted position as a function of time data is delayed, for example with a delay time of about 10 minutes to about 30 days, such as from about 1 hour to about 24 hours.

In the above embodiment where the means for acquiring and transmitting position as a function of time data of a movable object to the computer comprises a recording medium the integrity monitoring system may operate by recording position as a function of time of a movable object and transmitting the recorded data to the computer e.g. wireless with a time delay. In one embodiment the integrity monitoring system operates by recording position as a function of time on a first recording medium for a certain length of time, terminating recording on the first recording medium and transmitting the recorded data to the computer e.g. wireless or e.g. by physically connecting the first recording medium (which may be a movable recording medium) to the computer. The system may be operated such that the transmission of the recorded data on the first recording medium to the computer is conditioned on vibration as a function of time data transmitted to the computer and/or on the possible malfunction/damage observed on the stationary structure. At the time or overlapping with the time of terminating recording on a first recording medium, recording on another recording medium may e.g. be started to obtain a full recording.

In that way not all positions as a function of time of movable object need to be transmitted to the computer, but the position as a function of time data can later on be examined for examinations of earlier incidents.

In one embodiment the integrity monitoring system comprises a recording medium for recording the transmitted position as a function of time data. This recording may be used for statistics for calibration and/or for later examination of an incident.

In one embodiment the computer comprises hardware and software comprising as least a processor for comparing the position as a function of time data with the vibration data correlated to same time such that it can be at least estimated if vibrations sensed by the vibration sensor at a given time were or comprised vibrations caused by a movable object, such as a vessel.

Hardware means in this connection is the physical medium of the computer, and software means computer programs. As mentioned above the hardware or parts thereof may be integrated in other parts of the integrity monitoring system, such as in the vibration sensor. The software to be used in the integrity monitoring system may be well known software applied to collect the various data, to comparing the vibration data with the position as a function of time data and preferably to provide an output of the result e.g. on a display, a monitor and/or via a printer.

In one embodiment the computer comprises or is in data communication with a monitor and or a printer for displaying received data and the result of the comparison of the vibration data with the position as a function of time data.

As mentioned above the integrity monitoring system may comprise a plurality of vibration sensors which may be identical or differ from each other.

The vibration sensor and optionally the software for the vibration sensor may preferably be selected such that the integrity monitoring system is capable of determining the direction of a vibration relative to the vibration sensor and/or relative to the stationary structure.

In one embodiment the integrity monitoring system comprises at least one optical fibre vibration sensor in the form of a distributed or quasi-distributed sensor. A quasi-distributed sensor should be taken to mean a sensor which is not a distributed sensor, but which can be applied to provide sensing output as had it been a distributed sensor.

The optical fibre vibration sensor and/or the computer may in one embodiment be adapted to acquire and optionally to process output signals from a plurality of selected length sections N of the optical fibre vibration sensor, the selected sections N preferably have each a length of at least about 1 m, such as up to about 50 m, such as from about 1 to about 10 m, the length of the respective sections is preferably substantially equal.

In the above embodiment the plurality of selected length sections N of the optical fibre vibration sensor may for example be arranged substantially systematically along the length of the optical fibre vibration sensor, thereby simplifying the calculation process to obtain the distributed vibration data. The length sections N may be overlapping sections, immediately adjacent sections or sections with a distance to each other.

In one embodiment the system comprises a sensor array e.g. in the form of an array of discrete sensors or in the form of a distributed or quasi-distributed fibre sensor. The computer may preferably be adapted to acquire and process the vibration data from the sensor array. In a preferred embodiment the computer comprises software for determining a direction, a distance and/or a speed of a vibration emitting object, where the vibration emitting object optionally is the movable object.

In a preferred embodiment the integrity monitoring system is arranged to perform a beam forming function on the vibration data from the sensor array or distributed or quasi-distributed sensor.

In one embodiment it is desired that the integrity monitoring system is arranged to perform a beam forming function i.e. a direction of the vibration (sound) can be calculated which allows for the direction estimation of an incoming sound wave.

Sensor arrays and calculation methods (software) are well known in the art and further description may e.g. be found in U.S. Pat. No. 7,415,117 and U.S. Pat. No. 7,369,459. The beam forming function may comprise a calculation based on a cross bearing method. Further information and examples about how to perform and optimise array processing may for example be found in "Optimum Array Processing (Detection, Estimation, and Modulation Theory, Part IV)" by Harry L. Van Trees (ISBN 0-471-09390-4).

According to the invention the integrity monitoring system comprises means for acquiring and transmitting position as a function of time data of a movable object comprising a transmitter to the computer when the movable object is within a selected distance to a monitoring site, where the monitoring site comprises the part of the stationary structure to be monitored. The monitoring site is preferably the site that is desired to monitor, and for simplifying the system the monitoring site may preferably be selected to be identical with the site occupied by the part of the stationary structure to be monitored. If several stationary structures are to be monitored by one integrity monitoring system, the monitoring site is preferably selected to be the smallest site that comprises all of the stationary structures to be monitored.

The selected distance to the monitoring site may be a distance in some directions or in all directions. If for example the stationary structure is a buried stationary structure, the selected distance does not need to comprise a selected distance below the stationary structure since it is very unlikely that a movable object should approach the stationary structure from below the buried stationary structure.

Furthermore the selected distance need not be the same in all directions, but may vary, for example such that the selected distance in the horizontal direction is larger than the selected distance in the vertical direction. The selection of the distance is preferably made in relation to the risk of damage from movable objects or related/connected elements.

The system is arranged such that when a movable object comprising a transmitter is within the selected distance, position as a function of time data can be acquired and transmitted to the computer. As long as the movable object is not within the selected distance, position as a function of time data may be disregarded and not be acquired and/or transmitted to the computer. Thereby not relevant position as a function of time data can be ignored by the system.

It should be observed that the selected distance may be selected so large that a large number of irrelevant positions as a function of time data are transmitted to the computer. In this situation it is desired that the computer comprises software for sorting the position as a function of time data.

The integrity monitoring system of the invention may be an onshore integrity monitoring system or an offshore integrity monitoring system. As it should be clear to the skilled person the detailed selected part of the onshore integrity monitoring system and the offshore integrity monitoring system may preferably be selected in relation to the type of system and in relation to whether or not it should be applied in water.

In a preferred embodiment the integrity monitoring system is an offshore integrity monitoring system, and the stationary structure is a submarine structure and the movable object is a vessel.

The term "vessel" is used herein to denote any kind of seagoing ship, boat or submarine capable of crossing and/or capable of navigating on the ocean, in canals, and/or in rivers. In one embodiment the vessels comprise at least all vessels over 300 t. In one embodiment the vessels comprise at least all vessels over 40 t, such as fishing boats of for example 25-100 m in length including trawlers.

The submarine structure may for example be as any of the stationary structure mentioned above which is applied offshore.

In one embodiment the submarine structure is a riser extending in substantially vertical direction in at least a section of the submarine structure. "Substantially vertical direction" should be seen in relating to the sea surface at still water and means in general that the riser is not applied on the seabed, trenched and/or buried and that it is not applied essentially perpendicular to the sea surface. In one embodiment the riser extends from the seabed to a sea surface station such as a ship or a platform.

In one embodiment the submarine structure comprises a flexible cable and/or a flexible pipe applied on the seabed, trenched and/or buried.

In the offshore integrity monitoring system of the invention the means for acquiring and transmitting position as a function of time data to the computer may preferably comprise acquiring data from an Automatic Identification System (AIS), the data being acquired directly from the transmitter of the vessel, via internet transmission, via a vessel traffic service (VTS) and/or via an external antenna, the transmitter of the vessel being a transponder.

The AIS is an international vessel tracking system. As from December 2004, the International Maritime Organization (IMO) requires all vessels over 300 t to carry an AIS transponder on board, which transmits their position, speed and course, among some other static information, such as vessel's identification, dimensions and voyage details.

The purpose of AIS was initially to help ships avoid collisions, as well as assisting port authorities to better control sea traffic. Generally the accepted AIS transponders on board vessels comprise a positioning system, such as LORAN-C or GPS (Global Positioning System) receiver, which collects position and movement details, and a VHF transmitter, which transmits this information and make this data available to the public domain. The AIS transponders may further be integrated with other electronic navigation sensors, such as a gyrocompass or a rate of turn indicator. Other vessels or base stations are able to receive this information, process it using simple software and display vessels locations on a chart plotter or on a computer.

AIS position data are available on the Internet through many governmental as well as privately operated geographic information systems, such as www.marinetraffic.com, www.vesseltracker.com, www.vtexplorer.com, and www.shiptracking.eu.

"A vessel traffic service (VTS)" is a marine traffic monitoring system established by harbours or port authorities. The purpose of VTS is to improve the safety and efficiency of navigation, safety of life at sea and the protection of the marine environment in the areas around the harbours and ports. VTS is governed by SOLAS Chapter V Regulation 12 together with the Guidelines for Vessel Traffic Services (IMO Resolution A.857 (20)) adopted by the International Maritime Organization on 27 Nov. 1997.

A VTS will normally have a comprehensive traffic image, which means that all factors influencing the traffic as well as information about all participating vessels and their intentions are readily available. By means of the traffic image, situations that are developing can be evaluated and responded upon.

In one embodiment of the offshore integrity monitoring system the position as a function of time data is acquired via the Internet to the computer.

In one embodiment the monitoring site is selected to be substantially identical with the site occupied by the part of the submarine structure to be monitored.

In one embodiment the monitoring site is selected to be an elongate area with a width of up to about 100 m, such ad up to about 10 m in the horizontal direction and perpendicular to the global direction of the submarine structure, and a height sufficient to comprise the submarine structure. The global direction of the submarine structure is the length direction of the submarine structure ignoring small bends along the length of 5 m or less.

In one embodiment of the offshore integrity monitoring system the selected distance to the monitoring site provides a selected horizontal area, the system is arranged such that the computer is acquiring position as a function of time data from vessels with transmitter within the selected horizontal area.

In one embodiment of the offshore integrity monitoring system the selected distance to the monitoring site is selected such that at least an average noisy 40 t vessel and/or a vessel emitting a vibration (sound) of about 100 db which is within sensing range of the vibration sensor is also within the selected distance.

In that way it can be ensured that when the vibration sensor detects an average noisy 40 t vessel, the position as a function of time data of the average noisy 40 t vessel is transmitted to the computer for being correlated with the detected vibration data.

In one embodiment the selected distance to the monitoring site is selected to be sufficiently large such that any vessel in a position where it is sensible by the vibration sensor (it is in a position where it is registrable by the vibration sensor) will be within the selected distance.

In general the most important vessels to have position as a function of time data from are approaching trawlers and fishing ships, because such vessels often have equipment drawn along the seabed, and furthermore it has often been observed that such vessels by mistake are sailing with their anchor drawn along the seabed. In such situations the submarine structures may be in high danger of being damaged. The selected distance of the offshore integrity monitoring system is therefore preferably selected such that the offshore integrity monitoring system can detect such trawlers and fishing ships in sufficient time to activate an alarm and preferably warn the vessels.

In this connection it should be observed that the sound velocity and the distance from which a given sensor can sense a vibration, depend at least slightly on the temperature of the water, the salt content of the water and turbulence and stream of the water. Unless otherwise specified the determination should therefore be determined at still water, at the average temperature and salt concentration of the water.

In most situations the average weather conditions, temperature, turbulence, salt concentration etc. are well known for a given area and the selected distance can be selected with a security margin, such that position as a function of time data for all vessels that is sensed by the vibration sensor can be transmitted to the computer.

In one embodiment the selected distance to the monitoring site corresponds to at least about 100 m from the submarine structure, preferably at least about 1 km from the submarine structure, preferably at least about 2 km from the submarine structure, more preferably at least about 5 km from the submarine structure. When the monitoring site is the site occupied by the submarine structure, the distance to the submarine structure is identical to the distance to the monitoring site.

The vibration sensor should preferably have a relative long range when the system is an offshore integrity monitoring system. Often it takes relatively long time to stop or turn a vessel, and in case of danger it is preferred that an alarm can be provided relatively early in relation to a potential damage. Furthermore, the vibration pattern offshore is often relatively stable and simple to identify, such that such noise can be filtered off. The burden of having long range/highly sensitive vibration sensors is often that such vibration sensors also capture a large amount of noise, but as mentioned this burden may be simple to overcome by filtering off the major amount or all of the noise.

In one embodiment the one or more vibration sensors are arranged to detect vibrations of an ordinary anchor drop and/or a draw of an anchor or a similar tool along the seabed within a distance of about 100 m from the submarine structure, preferably within a distance of about 500 m from the submarine structure. Thereby it may be possible to set off an alarm in sufficient time to prevent damage from an approaching vessel with an anchor or other equipment drawn along the seabed.

In one embodiment the one or more vibration sensors are arranged to detect vibrations about 500 Hz at the monitoring site with a level down to about 30 db, preferably down to about 10 db, more preferable of down to about 3 db or even down to about 1 db.

Generally the fibre optic sensors known today are less sensitive than the most effective hydrophones. However, for most vibration sensors a detection range for vibrations in the range from about 50 Hz to about 1 kHz will be about 2 km or more for detection of the vibration (sound) provided by an average 40 t vessel, and/or a vessel emitting a vibration (sound) of amount 100 db.

By providing a plurality of vibration sensors and arranging a beam forming thereof the detection range can be increased and the sensitivity of the monitoring system can be increased as well.

In one embodiment it is desired that the detection range around the submarine structure and the monitoring site is at least about 1 km, such as at least about 2 km and preferably up to about 10 km For a frequency of 500 Hz the damping of sandy sea bottom is expected to be about 0.12 dB/m. The sound speed ratio at the water-sediment interface is in the 1.04-1.08 range. Sound velocity in water is about 1470 m/s.

In one embodiment of the offshore integrity monitoring system the one or more vibration sensors are arranged to detect vibrations from about 50 Hz to about 1 kHz at the monitoring site with a level down to about 30 db, preferably down to about 10 db, more preferable of down to about 3 db or even down to about 1 db.

In one embodiment of the offshore integrity monitoring system the one or more vibration sensors are arranged to detect vibrations of about 500 Hz to about 1 kHz at a level down to about 100 db caused by a vessel at still waters when the vessel is within a range of about 2 km from the submarine structure, preferably when the vessel is within a range of about 4 km from the submarine structure, preferably when the vessel is within a range of about 6 km from the submarine structure, preferably when the vessel is within a range of about 10 km from the submarine structure.

As mentioned above the vibration sensor may be arranged at a distance from the stationary structure, in contact with the stationary structure or optionally integrated in the stationary structure. In one embodiment of the offshore integrity monitoring system the vibration sensor is mounted at a mounting distance of the submarine structure.

The mounting distance may in principle be as large as desired provided that the vibration sensor is capable of sensing vibrations from the monitoring site. The mounting distance may for example be up to about 1 km, such as up to about 500 m, such as up to about 100 m, such as up to about 25 m. In one embodiment the mounting distance is between about 1 m and about 100 m.

In one embodiment of the offshore integrity monitoring system the vibration sensor is in contact with or integrated in the submarine structure.

"In contact with" is used herein to mean in physical contact with e.g. by being mounted or simply placed in contact.

Preferably the computer of the offshore integrity monitoring system comprises hardware and software comprising as least a processor for comparing the position as a function of time data with the vibration data correlated to same time such that it can be at least estimated if vibrations sensed by the vibration sensor at a given time were or comprised vibrations caused by an identified vessel.

Generally it is desired that the offshore integrity monitoring system comprises at least one memory e.g. one or more memories as described above.

In one embodiment the computer comprises or is in data communication with a database memory. A database memory should herein be interpreted to be a memory comprising or arranged to comprise a database. A database is to be interpreted as an organized collection of data which can be used by one or more users. The database memory preferably stores at least some of the vibration as a function of time data and/or some of the position as a function of time data acquired by the computer.

The offshore integrity monitoring system of the invention may thereby build up a database of at least some of the vibration as a function of time data and/or some of the position as a function of time data acquired by the computer, and the database may be used e.g. for calibration of the system, for predicting incidents, for regulating conditions for activation of an alarm or for other things.

In one embodiment the system comprises a database memory in data communication with the computer and the database memory comprises a calibration curve for vibration pattern versus vessel distance for one or more vessels or types of vessels, the computer comprises software for calculating the distance to a passing vessel.

In one embodiment the submarine structure comprises a buried or trenched submarine structure and the system comprises a database memory in data communication with the computer, where the database memory comprises a calibration curve for vibration pattern versus vessel distance for one or more vessels or types of vessels.

It may be desired that the integrity monitoring system is capable of recognising a vibration pattern. For example in a situation where a vessel is repeatedly e.g. regularly passing a buried or trenched submarine structure, and the vibration sensor is buried or trenched with or besides the submarine structure, the offshore integrity monitoring system may detect a change in vibration level in case the level of covering material has changed. If the offshore integrity monitoring system can recognise the vibration pattern, optionally calculate the direction, speed and other, the computer of the offshore integrity monitoring system may preferably comprise software for calculating the change of level of covering material above the submarine structure.

Thereby the offshore integrity monitoring system may be capable of calculating and/or predicting if and when the level of covering material is or becomes insufficient, and additional covering material may be applied prior to damage of the submarine structure e.g. to prevent damage of the submarine structure.

In one embodiment where the means for determining and transmitting position as a function of time data to the computer comprises acquiring data from an Automatic Identification System (AIS), the computer is arranged to acquire additional data from the AIS or from another source. The computer may for example be arranged to acquire one or more of unique identification, course, speed, direction of movement, warnings, weather conditions and predictions/forecasts of the mentioned data. Generally it is desired that the additional data at least comprises a unique identification of the vessel.

Information about weather conditions may for example comprise wind direction and velocity data as well as information about thunder. The weather condition data may e.g. be provided directly via internet.

Information about weather conditions may for example predict potential risks by anchoring during high wind situations, and an alarm may be triggered.

It may be that certain weather conditions decrease/increase the sensitivity of the vibration sensor. The weather conditions or forecasts of weather conditions can therefore in one embodiment be applied to regulate the activating set point for an alarm, in other words, the activating set point of the alarm depends on the weather.

Irrespectively of from which source the position as a function of time data is acquired, the integrity monitoring system may be arranged to collect weather related data, such as weather forecasts and/or weather related statistics and/or data related to weather conditions as a function of time.

The weather related statistics and/or data related to weather conditions as a function of time can for example be used to predict how an integrity monitoring system will react on various types of weather and/or to provide an improved weather forecasts, which again can be used in regulating one or more elements of the integrity monitoring system.

In one embodiment the computer comprises software for calculating a potential danger of damaging of the submarine structure by a vessel or vessel equipment. This calculation may for example be based on at least some of the vibration data and the position as a function of time data and optionally other data from a database memory, such as for example weather related data and/or speed, direction of movement and/or course of the moving object.

In one embodiment of the offshore integrity monitoring system the computer comprises software for associating at least some of the vibration data, with a potential danger of damaging of the submarine structure by a vessel or vessel equipment. Thereby an alarm can be activated when danger is estimated, calculated or in other ways predicted.

In one embodiment the system comprises an alarm arranged to be activated upon potential or actual danger of damaging of the submarine structure. The computer may preferably be arranged to calculate the potential or actual danger of damaging of the submarine structure. This calculation may preferably be based on at least some of the vibration data and at least some of the position as a function of time data. In one embodiment the system is regulated to activate the alarm upon detection of vibration data with a predefined pattern and/or with a vibration level above a max-level set-point. Thereby the risk of setting of false alarm can be highly reduced and a more reliable alarm system is obtained.

In one embodiment one or more of the following cases are evaluated as alarms.

Detection of an unusually low-speed vessel with or without changing direction.

Unusually high vibration level.

Very high vibration level which cannot be correlated to a specific movable object.

Vibration/noise with no AIS data available.

Steady increase of vibration level over time-period of e.g. 1 month/6 months/1 year for a certain part of a submarine structure.

In one embodiment the integrity monitoring system is an onshore integrity monitoring system. In this embodiment the stationary structure is a non-submarine structure, e.g. any of the above mentioned stationary structures applied onshore. The stationary structure preferably comprises a cable and/or a pipe.

In one embodiment of the onshore integrity monitoring system the stationary structure is buried or is supported on one or more pylons.

In the onshore integrity monitoring system the movable object may be any kind of movable object which is movable onshore and which comprises a transmitter for transmitting position as a function of time data. The movable object may for example be a vehicle, an airplane, and/or motorized tool.

In the situation where the stationary structure is a transmitting stationary structure, e.g. a pipe, a cable and/or a fibre, the movable object may for example be an industrial vehicle, a tractor, a vehicle with digging tools and or a motorized digging tool such as a drill.

Preferably the movable object comprises or is connected to a positioning system, such as GPS (Global Positioning System) position and optionally movement details, and a transmitter, arranged to transmit the data to the computer, preferably together with a unique identification of the movable object.

In one embodiment of the onshore integrity monitoring system the system comprises a transponder for receiving the position as a function of time data and for transmitting the data to the computer optionally wireless and/or via the internet, the transponder optionally additionally is capable of receiving and transmitting the vibration data.

In one embodiment of the onshore integrity monitoring system the system is arranged such that the computer is acquiring position as a function of time data from movable objects with transmitter within the selected distance to the monitoring site. The computer may e.g. acquire the position as a function of time data directly from the movable object via its transmitter.

In the onshore integrity monitoring system of the invention the selected distance is preferably relatively short, in particular if the stationary structure is arranged as a relatively noisy environment.

In one embodiment of the onshore integrity monitoring system the selected distance to the monitoring site corresponds to at least about 10 m from the stationary structure, preferably at least about 100 m from the submarine structure, preferably at least about 500 m from the submarine structure.

In one embodiment of the onshore integrity monitoring system the selected distance to the monitoring site is least about 10 m, preferably at least about 100 m, preferably at least about 500 m from the submarine structure.

In one embodiment the selected distance may vary from one type of movable object to another type of movably object. For example in one embodiment the selected distance for a drill may be about 20 cm and the selected distance for an industrial vehicle may be about 10 m.

In one embodiment of the onshore integrity monitoring system wherein the movable object in a motorized tool, the selected distance to the monitoring site is from about 5 cm to about 5 m, such as from 5 cm to about 1 m, such as from about 10 cm to about 50 cm.

In one embodiment of the onshore integrity monitoring system the one or more vibration sensors are arranged to detect vibrations from about 50 Hz to about 1 kHz at the monitoring site with a level down to about 30 db, preferably down to about 10 db, more preferable of down to about 3 db or even down to about 1 db.

In one embodiment of the onshore integrity monitoring system the vibration sensor is mounted at a mounting distance of the stationary structure. The mounting distance may for example be up to about 100 m, such as up to about 25 m. In highly noisy environment the mounting distance should preferably be relatively short.

In one embodiment of the onshore integrity monitoring system the vibration sensor is in contact with or integrated in the stationary structure.

In one embodiment of the onshore integrity monitoring system the computer comprises hardware and software comprising as least a processor for comparing the position as a function of time data with the vibration data correlated to same time such that it can be at least estimated if vibrations sensed by the vibration sensor at a given time were or comprised vibrations caused by an identified movable object.

In one embodiment of the onshore integrity monitoring system the computer comprises or is in data communication with a database memory. The database memory may preferably store at least some of the vibration as a function of time data and/or at least some of the position as a function of time data acquired by the computer.

In one embodiment of the onshore integrity monitoring system the computer is arranged to acquire additional data, the additional data comprises at least one of unique identification, course, speed, direction of movement, warnings, weather conditions and predictions/forecasts of the mentioned data. The additional data may preferably at least comprise unique identification.

The additional data and the database may be applied in a corresponding way as described above for the onshore integrity monitoring system.

In one embodiment of the onshore integrity monitoring system the computer comprises software for calculating a potential danger of damaging of the stationary structure by a movable object or equipments associated with such movable object. The calculation may preferably be based on at least some of the vibration data and some of the positions as a function of time data and optionally other data from a database memory, e.g. the types of data describe or mentioned above.

The onshore integrity monitoring system may comprise an alarm in a similar way as described for the offshore integrity monitoring system and the alarm may be set to operate in a similar manner.

In one embodiment of the onshore integrity monitoring system the system comprises an alarm arranged to be activated upon potential or actual danger of damaging of the stationary structure, the computer is arranged to calculate the potential or actual danger of damaging of the stationary structure, preferably based on at least some of the vibration data and at least some of the position as a function of time data. The system may preferably be regulated to activate the alarm upon detection of vibration data with a predefined pattern and/or with a vibration level above a max-vibration set-point for reduction of false alarm.

As indicated above, a plurality of integrity monitoring systems can be connected or combined for example such that a central surveillance of the integrity monitored stationary structure can be performed. The plurality of integrity monitoring systems may for example be combined such that their computers of the respective integrity monitoring systems are placed at a central spot for managing centrally. In one embodiment the plurality of integrity monitoring systems are combined by sharing part or parts with each other, the plurality of integrity monitoring systems may for example share a common central computer.

The invention also relates to a method of monitoring integrity of at least a part of a stationary structure. The method of the invention comprises
  (i) providing at least one vibration sensor for sensing vibration as a function of time;
  (ii) providing a computer;
  (iii) providing transmitting means for transmitting vibration data from the vibration sensor to the computer;
  (iv) arranging the vibration sensor to sense vibrations within a monitoring site comprising at least the part of the stationary structure;
  (v) acquiring position as a function of time data of a movable object comprising a transmitter when the vessels are within a selected distance to the monitoring site;
  (vi) providing the computer to process the vibration data and the position as a function of time data software for comparing the vibration data with the position as a function of time data.

Examples of the above have already been described above. Further it is preferred that the method of the invention comprises using an integrity monitoring system as described above.

The individual elements as well as combinations thereof may be as described above.

In one embodiment of the method of the invention the stationary structure is a submarine structure laid on the seabed or a buried and/or a trenched submarine structure or the stationary structure is a non-submarine structure. According to the invention the method comprises determining the integrity of at least a part of the stationary structure.

As mentioned above, in a preferred embodiment the stationary structure is or comprises a cable, such as a signal and/or a power transmission cable, preferably selected from a high voltage electric power cable (above about 72 kV e.g. up to about 550 kV or even higher), a medium voltage electric power cable (about 10-72 kV), a super conducting cable, an optical fibre cable and/or a communication cable.

In one embodiment of the method of the invention the vibration sensor operates continuously or at predetermined intervals, and the integrity monitoring system comprises a regulating function for regulating the operation of the vibration sensor, the method comprises manually, semi-automatically or automatically regulating the operation of the vibration sensor, for example in relation to the amount of noise, in relating to the number of movable objects within the selected distance, in relating to weather, in relation to time (night/day/working day/holiday . . . etc.) and/or in relation to other.

In one embodiment of the method of the invention the regulating function is an automatically or semi-automatically regulating mechanism, and the method comprises regulating the sensitivity of the vibration sensor, preferably in dependence on the concentration of vibrations within the selected distance of the monitoring site.

In one embodiment of the method of the invention the method comprises filtering off noise, preferably at least a part of background noise is filtered off. Methods of filtering off noise are well known to a skilled person.

In one embodiment of the method of the invention the method comprises recording the position as a function of time data of a movable object and preferably the recorded data are or can be used for later analysis of an event.

If for example a monitored stationary structure suddenly is subjected to damage the recorded position as a function of time data preferably in combination with recorded vibration data can be used for analysing the accident and optionally identifying the movable object. For example it may be that the operator of the movable object has ignored an alarm and that damage may be claimed from the operator or the owner of the movable object.

In one embodiment of the method of the invention the method comprises that the computer compares the position as a function of time data with the vibration data correlated to same time, and based on this correlation estimates if vibrations sensed by the vibration sensor at a given time were or comprised vibrations caused by a movable object.

In one embodiment of the method of the invention the method comprises determining the direction of a vibration relative to the vibration sensor and/or relative to the stationary structure. The method of determining the direction of vibration may for example be as described above.

In one embodiment of the method of the invention the system comprises a sensor array e.g. in the form of an array of discrete sensors or in the form of a distributed or quasi-distributed fibre sensor, the method comprises determining a direction, distance and/or speed of a vibration emitting object, the vibration emitting object optionally being the movable object.

In one embodiment of the method of the invention the method comprises beam forming the vibration data from the sensor array, e.g. as described above.

In one embodiment of the method of the invention the integrity monitoring system is an offshore integrity monitoring system, the method comprises determining the integrity of at least a part of a submarine structure.

In one embodiment of the method of the invention the method comprises that the computer is in communication with an Automatic Identification System (AIS).

In one embodiment of the method of the invention the system is an offshore integrity monitoring system, and the method comprises comparing the position as a function of time data with the vibration data correlated to same time, such that it can be at least estimated if vibrations sensed by the vibration sensor at a given time were or comprised vibrations caused by an identified vessel.

In one embodiment of the method of the invention the method comprises storing at least some of the vibrations as a function of time data and at least some of the positions as a function of time data acquired by the computer on a database memory, and thereby building a collection of data for example as described above. The method of the invention may additional comprise using the database e.g. as mentioned or described above.

In one embodiment of the method of the invention the method comprises obtaining and/or acquiring additional data, the additional data may be as described above and e.g. comprise at least one of unique identification, course, speed, direction of movement, warnings, weather conditions and predictions/forecasts of the mentioned data.

In one embodiment of the method of the invention the method comprises calculating a potential danger of damaging of the stationary structure by a movable object or equipment associated with a movable object. The calculation is preferably based on at least some of the vibration data and the position as a function of time data and optionally other data from a database memory e.g. any of the data mentioned above.

In one embodiment of the method of the invention the method comprises associating the vibration data, and in particular the vibration data comprising high vibration level, with a potential danger of damaging of the stationary structure, such as a submarine structure by a movable object or equipment associated with a movable object, such as a vessel or vessel equipments.

In one embodiment of the method of the invention the method comprises activating an alarm e.g. as described above. The alarm may for example be activated upon potential or actual danger of damaging of the stationary structure. The computer is preferably arranged to calculate the potential or actual danger of damaging of the stationary structure, preferably based on at least some of the vibration data and at least some of the position as a function of time data. The method of the invention preferably comprises regulating the system to activate the alarm upon detection of vibration data with a predefined pattern and/or with a vibration level above a max-vibration set-point for reduction of false alarm.

In one embodiment of the method of the invention the method comprises calibrating the vibration data for normal vibration pattern of the stationary structure.

In one embodiment of the method of the invention where the system is an offshore system and comprises a database memory in data communication with the computer, the database memory comprises a calibration curve for vibration pattern versus vessel distance for one or more vessel or type of vessels, and the method comprises calculating the distance to a passing vessel and/or calculating change of level of covering material above the submarine structure e.g. as described above.

BRIEF DESCRIPTION OF DRAWINGS

The invention will be explained more fully below in connection with a preferred embodiment and with reference to the drawings in which.

The figures are schematic and may be simplified for clarity. Throughout, the same reference numerals are used for identical or corresponding parts.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
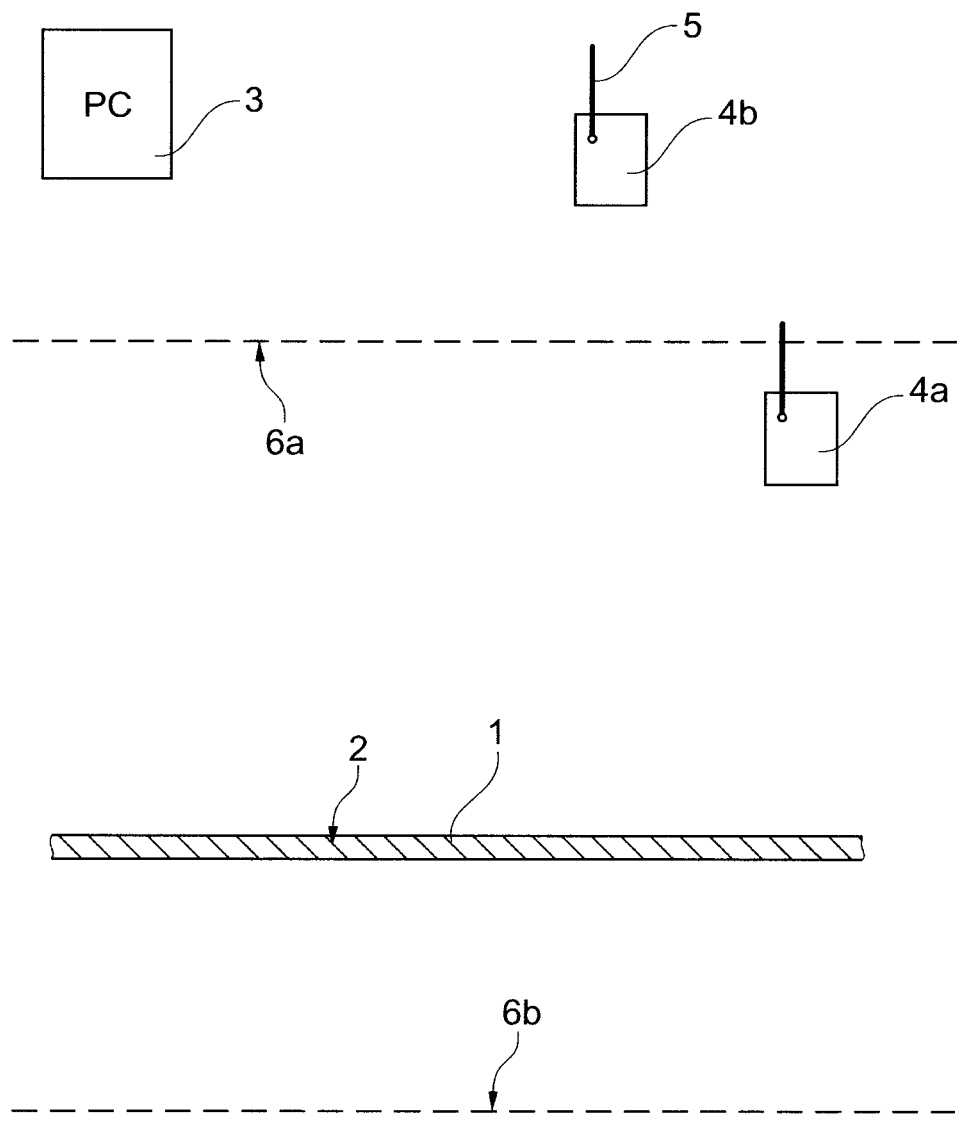
FIG. 1 is a schematic illustration of a part of an integrity monitoring system of the invention where the stationary structure is a section of a pipe.

The integrity monitoring system shown in FIG. 1 is adapted to monitoring the integrity of at least a length section of a pipe 1. The integrity monitoring system comprises a fibre sensor 2 helically wound around the pipe 1. The fibre sensor is or comprises a vibration sensor for example as described above. The fibre sensor is connected to not shown sensor system for feeding light to the sensor and for receiving and optionally analysing the resulting signals. The integrity monitoring system also comprises a computer 3, which is in this embodiment illustrated as a personal computer, but as explained the computer may be any other element or combination of elements that can perform the prescribed computing. The integrity monitoring system comprises not shown transmitting means for transmitting vibration data from the vibration sensor 2 to the computer 3.

This transmitting means may be provided by a direct connection of the fibre sensor 2 to the computer 3, by wireless transmission and/or by any other means e.g. as described above.

The integrity monitoring system further is arranged to acquiring and transmitting position as a function of time data of movable objects 4a, 4b comprising a transmitter 5 to the computer 3 when the movable objects 4a are within a selected distance 6a, 6b, here illustrated with dotted lines, to a monitoring site which is in this embodiment the site occupied by the pipe 1.

The movable objects 4a, 4b may for example be vehicles and/or tools e.g. as described above. The movable objects 4a, 4b comprises antennas 5 by use of which they can transmit their position data or position as a function of time data e.g. directly to be received by the computer 3 or via another system such as the internet or a central data collecting system, which can transmit the position as a function of time data further on to the computer 3.

As illustrated the selected distance 6a, 6b to the monitoring site need not be equidistant in all direction from the monitoring site, but may often be larger in one direction (for example the direction from the monitoring site and in the direction to the selected distance 6a) from the monitoring site than in another direction (for example the direction from the monitoring site and in the direction to the selected distance 6b) from the monitoring site.

The computer is in this embodiment prescribed and programmed to compare the vibration data with the position as a function of time data and thereby estimate if the movable object 4a within the selected distance 6a, 6b is in risk of damage the pipe 1.

Figure 2:
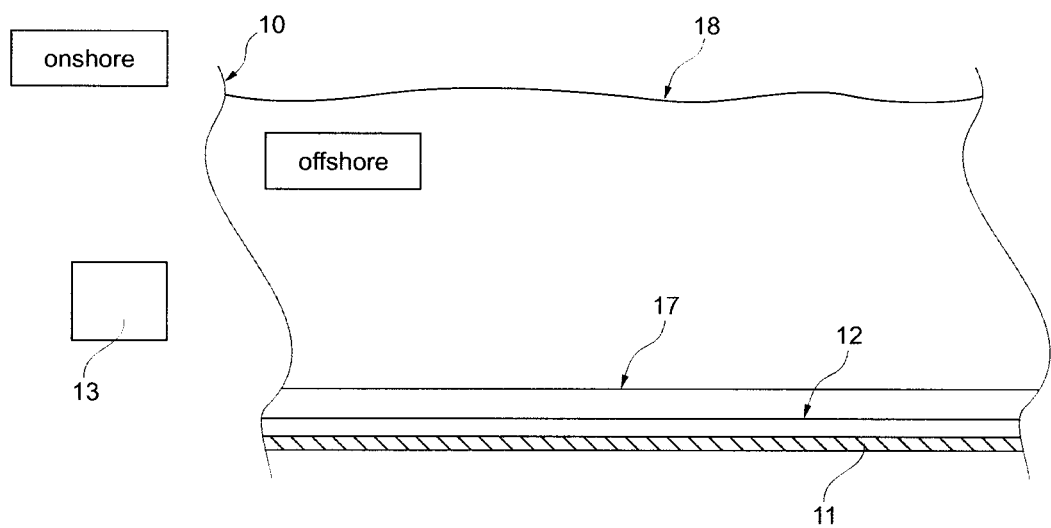
FIG. 2 is a schematic illustration of an offshore integrity monitoring system of the invention.

The integrity monitoring system shown in FIG. 2 is an offshore integrity monitoring system and is adapted to monitoring the integrity of at least a length section of the buried cable 11. The buried cable 11 is covered with covering material at the seabed 17. Right above the cable 11, is a vibration sensor 12 in the form of a fibre sensor buried. The fibre sensor 12 is connected to not shown sensor system for feeding light to the sensor and for receiving and optionally analysing the resulting signals. The line 10 illustrates a line between onshore and offshore. The line 18 illustrates the sea surface. The offshore integrity monitoring system comprises a computer 13 as disclosed above. This computer 13 is in this embodiment arranged onshore e.g. in a central surveillance site where optionally several integrity monitoring systems of the invention are kept under surveillance. The transmissions of vibration data/vibration as a function of time data and position as a function of time data may be performed as described above.

Figure 3:
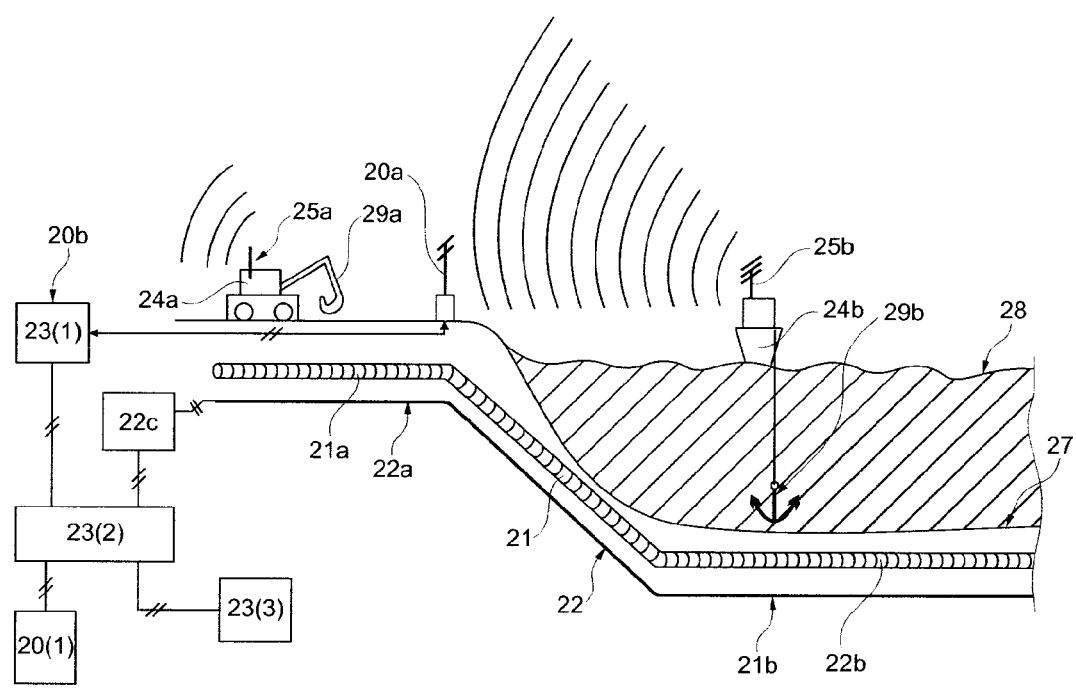
FIG. 3 is a schematic illustration of a combined offshore and onshore integrity monitoring system of the invention.

FIG. 3 shows a combined offshore and onshore integrity monitoring system of the invention. The combined onshore/offshore integrity monitoring system is adapted to monitoring the integrity of at least a length section of a pipe 21 comprising an onshore pipe section 21a and an offshore pipe section 21b. The onshore part of the integrity monitoring system comprises a data acquiring element 20a comprising a receiver and transmitter for receiving signals from onshore movable objects 24a and optionally from offshore movable objects 24b. In the shown embodiment an onshore movable object 24a is illustrated as a working vehicle with a digging tool 29a and a transmitter 25a, and an offshore movable objects 24b is shown as a vessel with a lowered anchor 29b and a transmitter 25b.

The offshore part of the integrity monitoring system comprises a not shown data acquiring element 20b arranged to acquire position as a function of time data from the AIS as described above. The position as a function of time data obtained from both the onshore data acquiring element 20a and the offshore data acquiring element 20b are transmitted to a first computer 23(1) where irrelevant position as a function of time data is sorted of and the relevant position as a function of time data optionally may be stored. The relevant position as a function of time data optionally in delayed form are transferred to a second computer 23(2) for further analyses as described below.

The combined offshore and onshore integrity monitoring system of the invention comprises a vibration sensor 22 in the form of a fibre sensor with an onshore vibration sensor section 22a and an offshore vibration sensor section 22b. The vibration sensor 22 is connected to a sensor system 22c for feeding light to the sensor and for receiving and optionally analysing and/or storing the resulting vibration signals. The vibration signals are transferred to the second computer 23(2) either in real time as vibration signals as such or in real time or delayed as vibration as a function of time data.

Additional data, such as weather related data or other as described above may be transmitted to the second computer 23(2) either via the onshore data acquiring element 20a and/or the offshore data acquiring element 20b and/or via another acquiring element 20(1).

The second computer 23(2) comprises software for comparing vibration as a function of time data with position as a function of time data relating to same time and based on this comparison and optionally additional data calculate risk of damage of the pipe 21, 21a, 21b onshore as well as offshore.

The second computer 23(2) is in the shown embodiment in data communication with a third computer 23(3) which is a surveillance computer and preferably comprises a monitor and an alarm indicator. Several integrity monitoring systems may be coupled to the same surveillance computer which may for example be kept under surveillance by an operator which e.g. also are keeping other surveillance computers under surveillance. If an alarm sets off the operator can immediately warn movable objects which may be in risk of damage a pipe. E.g. if a captain on a vessel 24b has forgot to take up his anchor 29b and it is draw over the seabed within the selected distance to the monitoring site, this may cause an alarm to go off, and the operator can immediately identify the vessel 24b and warn the captain, such that the captain can take up the anchor 29b before it is damaging the pipe 22b.

Figure 4:
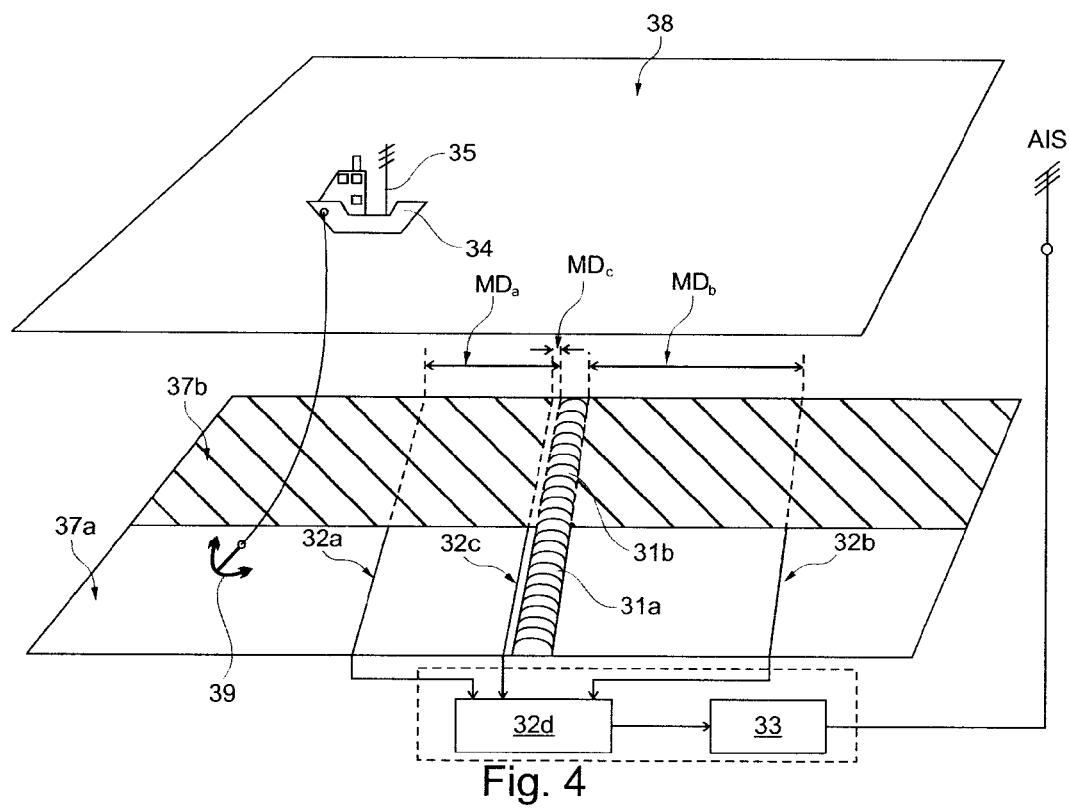
FIG. 4 is a schematic illustration of an offshore integrity monitoring system of the invention where the system comprises several fibre sensors and the submarine structure is partly buried and partly uncovered.

FIG. 4 illustrates an offshore integrity monitoring system seen in a perspective view. The plane 38 illustrates the sea surface and the plane 37a, 37b illustrates the seabed. The offshore integrity monitoring system comprises 3 optical vibration sensors 32a, 32b, 32c arranged parallel to a pipe 31a, 31b to be integrity monitored. The shown distances MDa, MDb, MDc indicates the mounting distances of respectively the vibration sensor 32a, 32b and 32c.

The vibration sensors 32a, 32b and 32c are connected to a sensor system 32d for feeding light to the sensor and for receiving and optionally analysing and/or storing the resulting vibration signals.

The offshore integrity monitoring system also comprises a computer 33. The computer 23 comprises hardware and software for acquiring position as a function of time data from the AIS as indicated on the drawing and as described above. The vibration signals obtained by the vibration sensors 32a, 32b and 32c are transferred to the computer 33 for analysing and comparing with the position as a function of time data as described above and optionally for recording the various data.

FIG. 4 further shows a vessel 34 with a transmitter 35 and an anchor 39.

As indicated by the hatched section 37b of the seabed 37a, 37b, a part of the pipe 31b and parts of the vibration sensors 32a, 32b and 32c are buried, whereas in the non hatched section 37a of the seabed 37a, 37b, the pipe 31a and the vibration sensors 32a, 32b and 32c are uncovered. The uncovered pipe section 31a may preferably be trenched in particular in the uncovering is a chosen arrangement.

Such uncovered pipe is relatively sensitive and can easily be damaged by an anchor which is drawn over the seabed. If the vessel 34 is approaching the pipe 31a, 31b in the non-covered area 31a, the sensor 32a closest to the anchor 39 of the vessel 34 will detect the anchor 39 and its direction of movement and will transfer the detected vibration data to the computer 33. The computer will also acquire position as a function of time data from the vessel 34, and by comparing these data it can be calculated if the pipe 31a is in danger of being damage by the anchor 39, and if so the vessel 34 can be warned.

If for example the uncovered part of the pipe is not an intentioned structure, but the covering material has been removed over time e.g. by vessels passing over the pipe 31 in a sailing channel, the offshore integrity monitoring system may comprises a database memory with a calibration curve for vibration pattern versus vessel distance for one or more vessels or types of vessels.

By using this calibration curve the integrity monitoring system is capable of recognising a vibration pattern, such that it can be detected if the pipe has uninterdentally been uncovered by passing vessels. If the offshore integrity monitoring system can recognise the vibration pattern, it may calculate the direction, speed and other, and the computer 33 of the offshore integrity monitoring system preferably comprises software for calculating the change of level of covering material above the submarine structure 31a, 31b.

Figure 5:
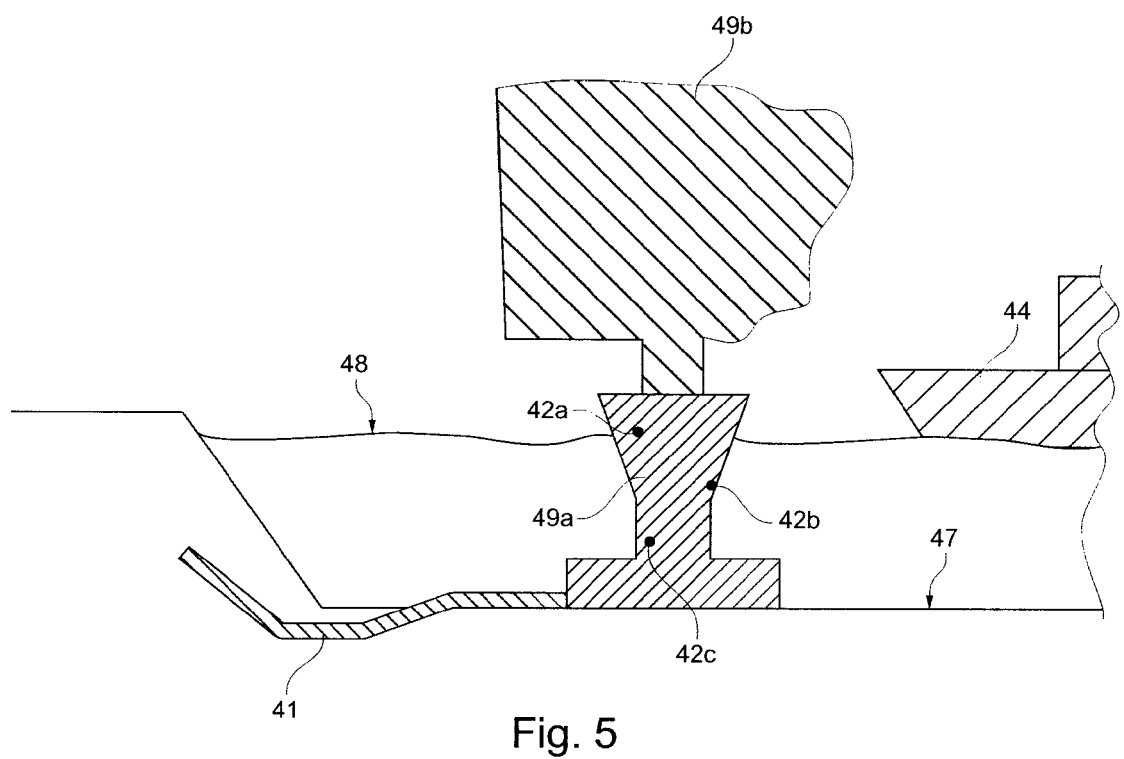
FIG. 5 is a schematic illustration of an offshore integrity monitoring system of the invention where the system comprises point sensors and the submarine structure is a riser

FIG. 5 shows a submarine structure 41 e.g. as described above (cable/pipe) connected to an offshore structure 49a, 49b, such as a platform placed on the seabed 47. The offshore structure 49a, 49b comprises a part 49a below sea surface 48 and a part 49b above sea surface 48. A number of point vibration sensors 42a, 42b, 42c are placed on the under sea surface part of the offshore structure 49a. A vessel 44 is approaching the offshore structure 49a, 49b, e.g. to berth to the offshore structure 49a, 49b.

The point vibration sensors 42a, 42b and 42c are a part of an integrity monitoring system of the invention and are transmitting vibration data to a not shown computer, where the vibration data is compared with position as a function of time data acquired from the AIS of approaching vessels.

In case the vessel 44 is in danger of damaging the submarine structure 41 the integrity monitoring system can set off an alarm as described above.

Figure 6:
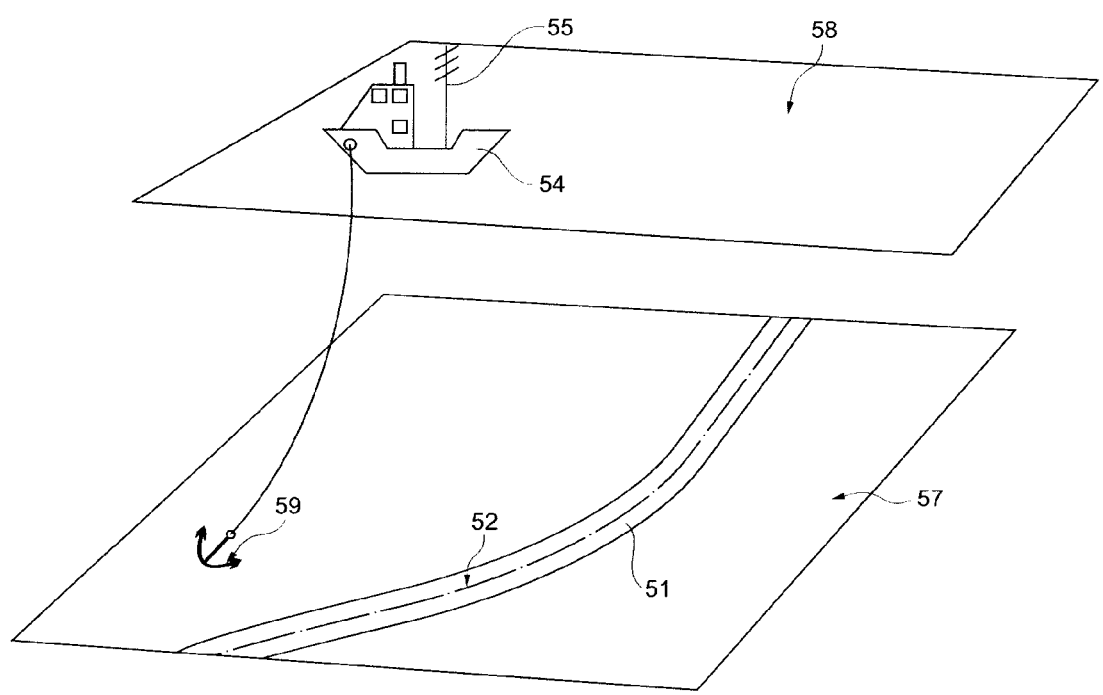
FIG. 6 is a schematic illustration of an offshore integrity monitoring system of the invention where the system comprises integrated sensors and the submarine structure is laid on the seabed.

FIG. 6 illustrates an offshore integrity monitoring system seen in a perspective view. The plane 58 illustrates the sea surface and the plane 57 illustrates the seabed. The offshore integrity monitoring system comprises an optical vibration sensor 52 (shown as a dotted line) integrated in the submarine structure 51. The submarine structure 51 is trenched, such that it does not protrude above the seabed 57.

The integrity monitoring system further comprises not shown computer, not shown transmitting means for transmitting vibration data from the vibration sensor 52 to the computer, not show means for acquiring and transmitting position as a function of time data of a movable object 54 comprising a transmitter 55 to the computer. In the shown embodiment, the movable object 54 is in the form of a vessel 54 and comprises a transmitter and an anchor 59, which is drawn over the seabed 57. The offshore integrity monitoring system operates as described above.

Figure 7:
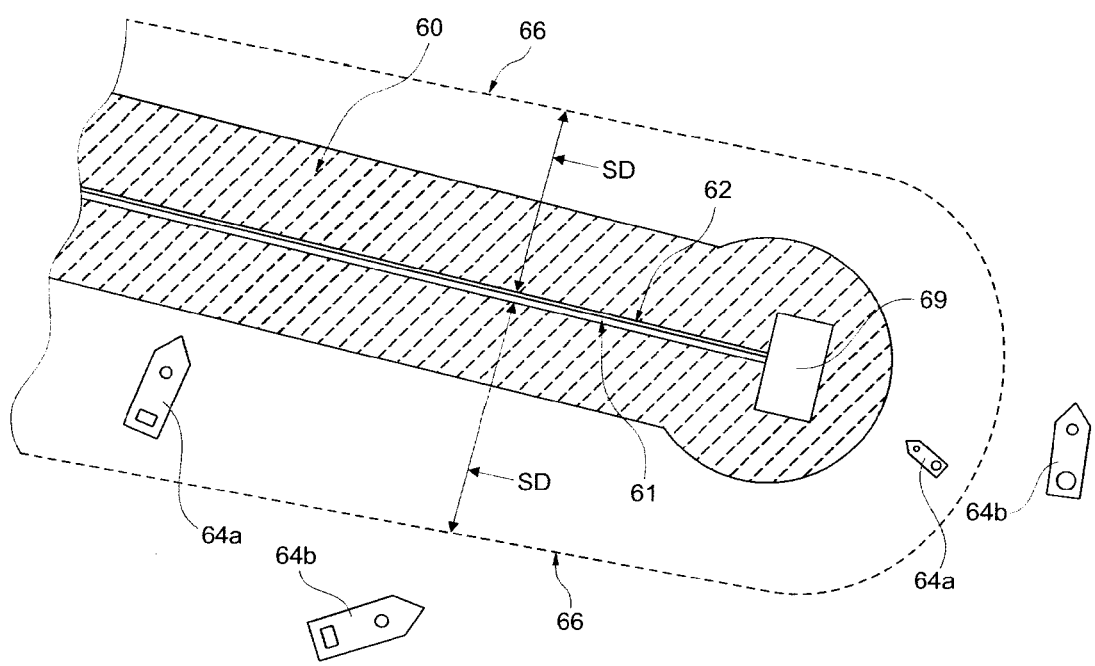
FIG. 7 is a schematic illustration of an offshore integrity monitoring system of the invention, seen from a distance from above, where a number of vessels are shown, some within the selected distance and some outside

The integrity monitoring system shown in FIG. 7 is adapted to monitoring the integrity of at least a length section of a submarine structure 61. The integrity monitoring system comprises a fibre vibration sensor 61 placed immediately adjacent to the submarine structure 61. The fibre vibration sensor may be as described above. The fibre vibration sensor is connected to not shown sensor system for feeding light to the sensor and for receiving and optionally analysing the resulting signals. The integrity monitoring system also comprises a not shown computer and various transmitting means and acquiring means as described above.

The submarine structure 61 and the sensor 62 is connected to an offshore structure 69, such as a platform e.g. as described in FIG. 4.

The integrity monitoring system is arranged to acquiring and transmitting position as a function of time data of movable objects 64a, 64b comprising not shown transmitters to the not shown computer when the movable objects 64a are within a selected distance SD, here illustrated with dotted lines 66, to a monitoring site which is in this embodiment the site occupied by the submarine structure 61.

As seen in FIG. 7 some of the vessels 64b are outside the dotted line 66 indicating the area within the selected distance SD to the monitoring site, and in this embodiment position as a function of time data fore these vessels 64b are outside the dotted line 66 will not be acquired and transmitted to the not shown computer, whereas the position as a function of time data for the vessels 64a within the selected distance SD, surrounded by the dotted line 66 will be acquired and transmitted to the not shown computer.

The hatched area 60 indicate a protection zone 60, and the integrity monitoring system is regulated such that an alarm is set off if/when an average noisy 40 t vessel or a vessel emitting sound of about 100 db is within the protection zone 60.

In a variation of the embodiment shown in FIG. 7 the elongate zone surrounded by the dotted line 66 is substantially parallel to the submarine structure and the submarine structure is applied in the middle axis thereof, preferably with the offshore structure 69 arranged substantially in the centre of the curved end of the elongate zone.

Figure 8:
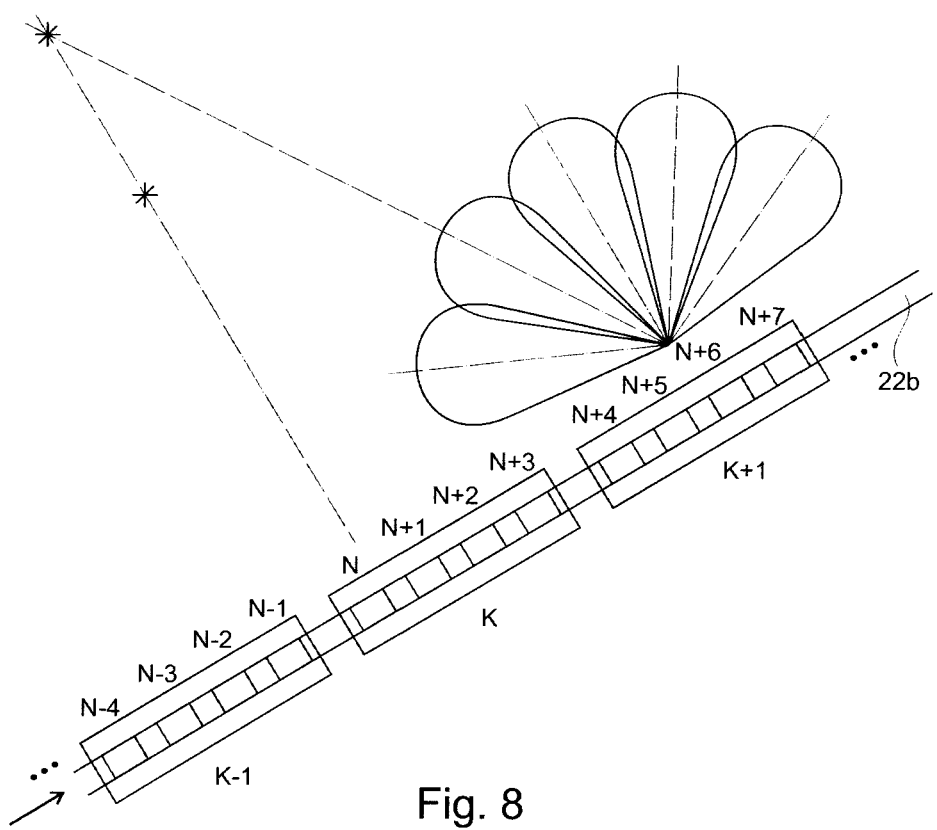
FIG. 8 is a schematic illustration of a vibration sensor and a principle of beamforming.

FIG. 8 shows a principle of beamforming which can be used in the integrity monitoring system of the invention.

The beamforming may e.g. be used in a method of estimating the distance between a stationary structure and a movable object or a noise emitting event by a movable object e.g. an anchor drop. The integrity monitoring system may for example be the integrity monitoring system shown in FIG. 3. When the vessel 24b drops the anchor 29b, the distance to the vessel 24b and the anchor 29b can be estimated/calculated using beamforming of the output signals of the fibre sensor 22b. The output signals are labelled by . . . , N−2, N−1, N, N+1, N+2, . . . in relating to length sections of the sensor 22b. A typical length of a section N is 1-10 m. The distance between the sections is fixed, typical values are 1-3 m.

The output signals of an array of a number of sections (e.g. 4) sections are processed together and space oriented signals (beams, e.g. 5) are generated for each array with number . . . , K−1, K, K+1, . . . . This allows for the direction estimation of an incoming sound wave.

If e.g. the anchor 29b is dropped on the sea bottom, the section with the highest output level is determined. If for example this section is number N belonging to array K. Then the output signals of an array in the vicinity of array K are analyzed and an estimate of the event distance is determined by cross bearing.

This method can for example be simplified for high signal-to-noise-ratios leaving out the array processing. If an anchor is dropped on the sea bottom, the section with the highest output level (N) is determined. The output signal of a second section (e.g. with number N+5) is analyzed and correlated with the output signal of section N. The time difference between the two signals is used to estimate the event distance.

Figure 9:
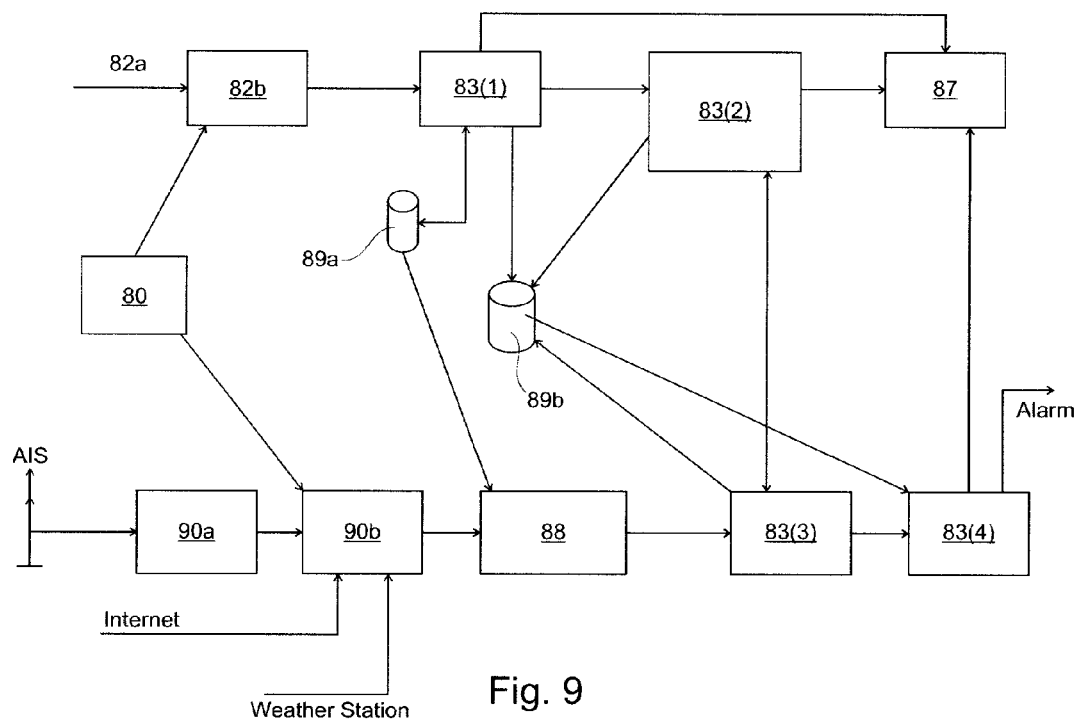
FIG. 9 is a schematic illustration of an embodiment of the method of the invention where the integrity monitoring system is an offshore integrity monitoring system.

FIG. 9 shows a diagram of a processing method of the invention. A vibration sensor 82a is connected to a sensor system 82b for feeding light to the sensor and for receiving the resulting vibration signals. Time data is acquired by the sensor system e.g. from a time setting unit 80 or from a not shown clock incorporated in the sensor system 82b. The vibration data is correlated with time data to provide vibration as a function of time data.

The vibration as a function of time data is transmitted to a first computer 83(1) where the vibration as a function of time data is sorted, optionally filtered to remove stationary noise and is further analysed e.g. by beamforming. The analysed vibration as a function of time data is transferred to a first database memory 89a. The first database memory 89a may also store the non analysed vibration as a function of time data.

The analysed vibration as a function of time data is also transferred to a second computer 83(2) where it is compared with other data.

Simultaneously a first data acquiring element 90a acquires position as a function of time data and optionally other data from the AIS. Time data is acquired by the first data acquiring element 90 e.g. from a time setting unit 80 or from a not shown clock incorporated in the sensor system 82b. The position as a function of time data is correlated with the acquired time data to ensure that the vibration data and position data correlates to harmonised time data.

The position as a function of time data is transmitted to a second data acquiring element 90b, which second data acquiring element 90b also acquires data from other sources, such as from the internet and from a weather station. The second data acquiring element 90b may also acquire time data as the first data acquiring element 90a.

The data from the second data acquiring element 90b are transmitted to a filter element 88, where irrelevant data are filtered of. The filter may be regulated in dependant of the data stored on the first database memory. Thereby the noise detected by the vibration sensor 82a influences which data are filtered off.

The filtered data are transmitted to a third computer 83(3). The second computer 83(2) and the third computer 83(3) is in one embodiment merged to one single computer and in another embodiment—the shown embodiment—the second computer 83(2) and the third computer 83(3) exchange data. In the second computer 83(2) the data are sorted and organised and transmitted to a second database memory 89b as well as to an operator monitor 87. In the third computer 83(3) the position as a function of time data and the vibration as a function of time data are compared and simultaneously other data are correlated to each other and in the same computer or in a fourth computer 84(4) (as in the shown embodiment), a threats evaluating are performed and the result is transmitted to the monitor. Simultaneously the fourth computer 84(4) may set off an alarm optionally after a confirmation of an operator, who is keeping the monitor 87 under surveillance.

The fourth computer 83(4) may also receive data from the second database memory 89b to evaluate the threats, or for performing supplementary analysis. The vibration as a function of time data may also be transmitted from the first computer 83(1) to the second database memory 89b and/or to the monitor 87.

The figures are schematic and may be simplified for clarity. Throughout, the same reference numerals are used for identical or corresponding parts.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Some preferred embodiments have been shown in the foregoing, but it should be stressed that the invention is not limited to these, but may be embodied in other ways within the subject-matter defined in the following claims.

What is claimed is:

1. An integrity monitoring system for monitoring integrity of at least a part of a stationary structure, the system comprising:
at least one vibration sensor for sensing vibration as a function of time,
a computer comprising a processor,
transmitting means for transmitting vibration data from the vibration sensor to the computer,
means for acquiring, via a transmitter of a movable object, and transmitting position as a function of time data of said movable object to said computer when said movable object is within a selected distance to a monitoring site,
wherein the monitoring site comprises the part of the stationary structure and the vibration sensor is arranged to sense vibrations within said monitoring site, said processor being programmed to execute instructions to compare the vibration data from the vibration sensor with the position as a function of time data from the transmitter of the movable object, and
wherein the means for acquiring and transmitting position as a function of time data is independent from the at least one vibration sensor.

2. The integrity monitoring system as claimed in claim 1, wherein the stationary structure comprises a cable, a pipe and/or an optical fibre.

3. The integrity monitoring system as claimed in claim 1, wherein the vibration sensor is an acoustic sensor configured to measure mechanical waves in liquids and/or solids.

4. The integrity monitoring system as claimed in claim 1, wherein the system comprises one or more redundant vibration sensors applied to replace malfunctioning vibration sensors and/or for testing active vibration sensors.

5. The integrity monitoring system as claimed in claim 1, wherein the vibration sensor comprises at least one hydrophone.

6. The integrity monitoring system as claimed in claim 1, wherein the vibration sensor is a distributed vibration sensor.

7. The integrity monitoring system as claimed in claim 1, wherein the vibration sensor comprises an optical fibre sensor.

8. The integrity monitoring system as claimed in claim 1, wherein the vibration sensor comprises a Fibre Bragg Gratings (FBGs) sensor.

9. The integrity monitoring system as claimed in claim 1, wherein the vibration sensor is integrated with or directly connected to the transmitting means.

10. The integrity monitoring system as claimed in claim 1, wherein the means for transmitting vibration data from the vibration sensor to the computer comprises a recording medium, the transmitted vibration data comprises the vibration as a function of time and the vibration as a function of time data being delayed.

11. The integrity monitoring system as claimed in claim 1, wherein the transmitting means for transmitting vibration data from the vibration sensor to the computer, is arranged to transmit vibration as a function of time data or it is arranged to transmit vibration data without time data and the time connected to the respective vibration data is generated by the system.

12. The integrity monitoring system as claimed in claim 1, wherein the means for acquiring and transmitting position as a function of time data of a movable object comprises a receiver capable of receiving the position as a function of time data directly from the transmitter of the movable object, via internet transmission, via satellite and/or via an external antenna.

13. The integrity monitoring system as claimed in claim 1, wherein the computer comprises hardware and software comprising as least a processor for comparing the position as a function of time data with the vibration data correlated to same time such that it can be at least estimated if vibrations sensed by the vibration sensor at a given time were or comprised vibrations caused by a movable object.

14. The integrity monitoring system as claimed in claim 1, wherein the system is adapted to determine the direction of a vibration relative to the vibration sensor and/or relative to the stationary structure.

15. The integrity monitoring system as claimed in claim 1, comprising at least one optical fibre vibration sensor, wherein the vibration sensor is a distributed or quasi-distributed sensor and the optical fibre vibration sensor and/or the computer is adapted to acquire and process output signals from a plurality of selected length sections N of the optical fibre vibration sensor, the system is arranged to perform a beam forming function on the vibration data from the sensor array or the distributed or quasi-distributed sensor.

16. The integrity monitoring system as claimed in claim 1, wherein the system comprises a sensor array, the computer is adapted to acquire and process the vibration data from the sensor array, the computer comprises software for determining a direction, distance and/or speed of a vibration emitting object, the vibration emitting object optionally being the movable object.

17. The integrity monitoring system as claimed in claim 1, wherein the integrity monitoring system is an offshore integrity monitoring system, the stationary structure is a submarine structure and the movable object is a vessel.

18. The integrity monitoring system as claimed in claim 17, wherein the submarine structure comprises a flexible cable and/or a flexible pipe applied on the seabed, trenched and/or buried.

19. The integrity monitoring system as claimed in claim 17, wherein the means for acquiring and transmitting position as a function of time data to the computer comprises acquiring data from an Automatic Identification System (AIS), the data being acquired directly from the transmitter of the vessel, via internet transmission, via a vessel traffic service (VTS) and/or via external antenna, the transmitter of the vessel being a transponder.

20. The integrity monitoring system as claimed in claim 17, wherein the selected distance to the monitoring site provides a selected horizontal area, the system is arranged such that the computer is acquiring position as a function of time data from vessels with transmitter within said selected horizontal area.

21. The integrity monitoring system as claimed in claim 17, wherein the vibration sensor is mounted at a mounting distance of the submarine structure.

22. The integrity monitoring system as claimed in claim 17, wherein the computer comprises hardware and software comprising as least a processor for comparing the position as a function of time data with the vibration data correlated to same time such that it can be at least estimated if vibrations sensed by the vibration sensor at a given time were or comprised vibrations caused by an identified vessel.

23. The integrity monitoring system as claimed in claim 17, wherein the means for determining and transmitting position as a function of time data to the computer comprises acquiring data from an Automatic Identification System (AIS), the computer is arranged to acquire additional data from the AIS or from another source, the additional data comprises at least one of unique identification, course, speed, direction of movement, warnings, weather conditions and predictions/forecasts of the mentioned data, preferably the additional data comprises at least unique identification.

24. The integrity monitoring system as claimed in claim 17, wherein the computer comprises software for calculating a potential danger of the damaging of the submarine structure by a vessel or vessel equipment, the calculation is based on at least some of the vibration data and the position as a function of time data and optionally other data from a database memory.

25. The integrity monitoring system as claimed in claim 17, wherein the system further comprises an alarm arranged to be activated upon potential or actual danger of damaging of the submarine structure.

26. The integrity monitoring system as claimed in claim 17, wherein the system comprises a database memory in data communication with the computer, the database memory comprises a calibration curve for vibration pattern versus vessel distance for one or more vessels or types of vessels, the computer comprises software for calculating the distance to a passing vessel.

27. The integrity monitoring system as claimed in claim 17, wherein the submarine structure comprises a buried or trenched submarine structure, the system comprises a database memory in data communication with the computer, the database memory comprises a calibration curve for vibration pattern versus vessel distance for one or more vessels or types of vessels, the computer comprises software for calculating a change of level of covering material above the submarine structure.

28. The integrity monitoring system as claimed in claim 1, wherein the integrity monitoring system is an onshore integrity monitoring system, the stationary structure is a non-submarine structure and the movable object is a vehicle, an airplane or a motorized tool.

29. The integrity monitoring system as claimed in claim 28, wherein the movable object comprises a positioning system.

30. The integrity monitoring system as claimed in claim 28, wherein the computer comprises hardware and software comprising as least a processor for comparing the position as a function of time data with the vibration data correlated to same time such that it can be at least estimated if vibrations sensed by the vibration sensor at a given time were or comprised vibrations caused by an identified movable object.

31. The integrity monitoring system as claimed in claim 1, wherein the position as a function of time data comprises geographical coordinates.

32. The integrity monitoring system as claimed in claim 1, wherein the position as a function of time data is uninfluenced by said vibration of a time data.

33. The integrity monitoring system as claimed in claim 1, wherein the position as a function of time data is acquires from an Automatic Identification System (AIS).

34. A method of monitoring integrity of at least a part of a stationary structure the method comprising the steps of:
  (i) providing at least one vibration sensor for sensing vibration as a function of time;
  (ii) providing a computer comprising a processor;
  (iii) providing transmitting means for transmitting vibration data from the at least one vibration sensor to the computer;
  (iv) arranging said at least one vibration sensor to sense vibrations within a monitoring site comprising at least the part of the stationary structure;
  (v) acquiring, via a transmitter of a movable object, position as a function of time data of the movable object when said movable object is within a selected distance to said monitoring site; and
  (vi) programming said processor to execute instructions to process said vibration data from the at least one vibration sensor and said position as a function of time data from the transmitter of the movable object and compare the vibration data with the position as a function of time data,
    wherein the transmitter of the movable object is independent from the at least one vibration sensor.

35. An integrity monitoring system for monitoring integrity of at least a part of a stationary structure, the system comprising at least one vibration sensor for sensing vibration as a function of time, a computer, transmitting means for transmitting vibration data from the vibration sensor to the computer, means for acquiring and transmitting position as a function of time data of a movable object comprising a transmitter to said computer when said movable object is within a selected distance to a monitoring site, where the monitoring site comprises the part of the stationary structure and the vibration sensor is arranged to sense vibrations within said monitoring site, said computer comprises hardware and software for comparing the vibration data with the position as a function of time data, wherein the integrity monitoring system is an offshore integrity monitoring system, the stationary structure is a submarine structure and the movable object is a vessel and wherein said one or more vibration sensors are arranged to detect vibrations about 500 Hz at the monitoring site with a level down to about 30 db.

* * * * *